(12) United States Patent
Dean et al.

(10) Patent No.: US 8,334,272 B2
(45) Date of Patent: Dec. 18, 2012

(54) METHODS FOR NUCLEIC ACID TRANSFER INTO CELLS

(75) Inventors: David A. Dean, Rochester, NY (US); Robert Christopher Geiger, Fort Myers, FL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 12/902,240

(22) Filed: Oct. 12, 2010

(65) Prior Publication Data
US 2011/0021608 A1    Jan. 27, 2011

Related U.S. Application Data

(63) Continuation of application No. 12/163,152, filed on Jun. 27, 2008, now abandoned.

(60) Provisional application No. 60/937,445, filed on Jun. 27, 2007.

(51) Int. Cl.
*A61K 31/70* (2006.01)
*C07H 21/02* (2006.01)
*C07H 21/04* (2006.01)
*C12P 19/34* (2006.01)
*C12Q 1/68* (2006.01)

(52) U.S. Cl. ......... 514/44; 536/24.5; 435/6.1; 435/91.1; 435/325; 435/375

(58) Field of Classification Search .............. 514/44
See application file for complete search history.

(56) References Cited

U.S. PATENT DOCUMENTS
5,459,127 A   10/1995  Felgner et al.

FOREIGN PATENT DOCUMENTS
| WO | 95/18863 | 7/1995 |
| WO | 95/21931 | 8/1995 |
| WO | 96/17823 | 6/1996 |
| WO | 96/25508 | 8/1996 |

OTHER PUBLICATIONS

Pamela Stanley Lab Wiki—Transfection, dated Jul. 28, 2004, pp. 1-4, downloaded on Jan. 11, 2011 from (http://stanxterm.aecom.yu.edu/wiki/index.php?page=Transfection).*
Arce et al. "Incorporation of L-Tyrosine, L-Phenylalanine and L-3, 4-Dihidroxyphenylalanine as Single Units into Rat Brain Tubulin." 1975, Eur. J. Biochem. 59:145-149.
L'Hernault & Rosenbaum, 1985, Biochem. 24:473-478.
Edde et al. 1990, Science 247:83-85.
Reed et al. "Microtubule Acetylation Promotes Kinesin-1 Binding and Transport." 2006, Curr. Biol. 16:2166-2172.
Haggarty et al. "Domain-selective small-molecule inhibitor of histone deacetylase 6 (HDAC6)-mediated tubulin deacetylation." 2003, Proc. Natl. Acad. Sci. 100:4389-4394.
Felgner et. al., "Lipofection: A highly efficient, lipid-mediated DNA-transfection procedure." Proc. Natl. Acad. Sci. USA, 1987, 84:7413-7417.

(Continued)

*Primary Examiner* — Terra Cotta Gibbs
(74) *Attorney, Agent, or Firm* — Casimir Jones, S.C.

(57) ABSTRACT

The present invention provides methods for increasing the transfer of nucleic acids into cells. In particular, the present invention provides for the use of inhibitors of HDAC6, a cytoplasmic histone deacetylase present in mammalian cells by, for example, small molecules or siRNA treatment, in increasing gene transfer and/or expression in cells in vitro and in vivo for research and gene therapy applications.

7 Claims, 20 Drawing Sheets

OTHER PUBLICATIONS

Mackey, et al., 1988, Proc. Natl. Acad. Sci. USA 85:8027-8031.
Ulmer et al., 1993, Science 259:1745-1748.
Felgner and Ringold, 1989, Nature 337:387-388.
Wu et al., 1992, J. Biol. Chem., 267:963-967.
Wu and Wu. "Recepto-mediated Gene Delivery and Expression in Vivo." 1988, J. Biol. Chem., 263:14621-14624.
Williams et al. "Introduction of foreign genes into tissues of living mice by DNA-coated microprojectiles." 1991, Proc. Natl. Acad. Sci. USA 88:2726-2730.
Curiel et al., 1992, Hum. Gene Ther., 3:147-154.
Wu and Wu. "Receptor-mediated in Vitro Gene Transformation by a Soluble DNA Carrier System." 1987, J. Biol. Chem., 262:4429-4432.
Machado-Aranda et al. "Gene Transfer of the Na+,K+-ATPase β1 Subunit Using Electroporation Increases Lung Liquid Clearance." Am J Respir Crit Care Med, 171: 204-211, (2005).
Dean, D.A. 2003. DNA Cell Biol, 22: 797-806.
Zhou et al. "Electroporation-mediated transfer of plasmids to the lung results in reduced TLR9 signaling and inflammation." Gene Ther, 14: 775-780, 2007.
X. Gao and L. Huang (1993). Cytoplasmic expression of a reporter gene by codelivery of T7 RNA polymerase and T7 promoter sequence with cationic liposomes. Nucleic Acids Res 21:2867-72.
Zabner, J. et al. (1995). Cellular and molecular barriers to gene transfer by a cationic lipid. J Biol Chem 270:18997-9007.
Kao, H.P. et al. (1993). Determinants of the translational mobility of a small solute in cell cytoplasm. J Cell Biol 120:175-84.
G. L. Lukacs et al. (2000). Size-dependent DNA mobility in cytoplasm and nucleus. J Biol Chem 275:1625-9.
Dauty, E. et al. (2005). Actin cytoskeleton as the principal determinant of size-dependent DNA mobility in cytoplasm: a new barrier for non-viral gene delivery. J Biol Chem 280:7823-8.
Birukov, K. G. et al. 2003. Magnitude-dependent regulation of pulmonary endothelial cell barrier function by cyclic stretch. Am J Physiol Lung Cell Mol Physiol 285(4):L785-L797.
Birukova, A. A. et al. 2005. MAP kinases in lung endothelial permeability induced by microtubule disassembly. Am J Physiol Lung Cell Mol Physiol 289(1):L75-L84.
Geiger, R. C. et al. 2006. Cyclic stretch-induced reorganization of the cytoskeleton and its role in enhanced gene transfer. Gene Ther 13(8):725-31.
Billger, M. et al. 1991. Microtubule-associated proteins-dependent colchicine stability of acetylated cold-labile brain microtubules from the Atlantic cod, Gadus morhua. J Cell Biol 113(2):331-318.
Hubbert, C. et al. 2002. HDAC6 is a microtubule-associated deacetylase. Nature 417(6887):455-8.
Matsuyama A. et al. 2002. In vivo destabilization of dynamic microtubules by HDAC6-mediated deacetylation. Embo J 21(24):6820-31.
Palazzo, A. et al. 2003. Cell biology: Tubulin acetylation and cell motility. Nature 421(6920):230.
Taylor, W. et al. (2003). The effects of cyclic stretch on gene transfer in alveolar epithelial cells. Mol Ther 7:542-9.
Zhang, Y. et al. (2003). HDAC-6 interacts with and deacetylates tubulin and microtubules in vivo. Embo J 22:1168-79.
Suzuki, T. et al. (2006). Highly potent and selective histone deacetylase 6 inhibitors designed based on small-molecular substrate. J Med Chem 49:4809-4812.
Vaughan, E. E. et al. (2006). Intracellular trafficking of plasmids during transfection is mediated by microtubules. Mol Ther 13:422-8.
Wilson, G. L. et al. (1999). Nuclear import of plasmid DNA in digitonin-permeabilized cells requires both cytoplasmic factors and specific DNA sequences. J. Biol. Chem. 274:22025-22032.
Kovacs, J. J. et al. (2005). HDAC6 regulates Hsp90 acetylation and chaperone-dependent activation of glucocorticoid receptor. Mol Cell 18:601-7.
Brush, M. H. et al. (2004). Deactylase inhibitors disrupt cellular complexes containing protein phosphatases and deacetylases. J Biol Chem 279:7685-91.
Kong, X. et al. (2006). Histone deacetylase inhibitors induce VHL and ubiquitin-independent proteasomal degradation of hypoxia-inducible factor 1alpha. Mol Cell Biol 26:2019-28.
Qian, D. Z. et al. (2006). Class II Histone Deacetylases Are Associated with VHL Independent Regulation of Hypoxia-Inducible Factor 1{alpha}. Cancer Res 66:8814-21.
Kim, S. H. et al. (2007) Regulation of the HIF-1alpha stability by histone deacetylases. Oncol Rep 17:647-51.
Kim, S. H. et al. (2007). Inhibition of hypoxia-induced angiogenesis by sodium butyrate, a histone deacetylase inhibitor, through hypoxiainducible factor-1alpha suppression. Oncol Rep 17:793-7.
Kwon et al. (2005). Biological function of the vaccinia virus Z-DNA-binding protein E3L: Gene transactivation and antiapoptotic activity in HeLa cells. PNAS 102:12759-12764.
Kwon et al. (2005). Biological function of the vaccinia virus Z-DNA-binding protein E3L: Gene transactivation and antiapoptotic activity in HeLa cells. Supporting information. PNAS 102:12759-12764.
Invitrogen, Lipofectamine 2000 Tranfection Reagent Product Description, downloaded from http://tools.invitrogen.com/Content/SFS/ProductNotes/F_Lipofectamin%202000b-040923-RD-MKT-TL-HL050602.pdf on Apr. 10, 2010.
Kim et al. (2006). Histone Deacetylase Inhibitor—Mediated Radiosensitization of Human Cancer Cells: Class Differences and the Potential Influence of p. 53. Clin Cancer Res 12(3):940-949.
Xue et al. (2003). Rational design, synthesis and structure-activity relationships of a cyclic succinate series of TNF-alpha converting enzyme inhibitors. Part 1: lead identification. Bioorg Med Chem Lett 13:4293-4297.
Suzuki et al. (2006). Highly potent and selective histone deacetylase 6 inhibitors designed based on a small-molecular substrate. J Med Chem 49:4809-4812.
Illies et al. (2004). Pyridinium cationic lipids in gene delivery: a structure-activity correlation study. J Med Chem 47:3744-3754.

\* cited by examiner

```
                           SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gcttctaact ggtccactat a                                            21

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggattgggat gttcatcatg g                                            21

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
ggactttaat acccaggatg t                                            21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gccttcctat tgacgtacat g                                            21
```

METHODS FOR NUCLEIC ACID TRANSFER INTO CELLS

The present application is a continuation of abandoned U.S. patent application Ser. No. 12/163,152, filed Jun. 27, 2008, which claims priority to U.S. Provisional Application 60/937,445, filed Jun. 27, 2007, each of which is herein incorporated by reference in its entirety.

STATEMENT REGARDING GOVERNMENT FUNDING

This invention was made with government support under Grant No. HL 071643 and HL 076139 awarded by the National Institutes of Health. The government has certain rights in the invention.

FIELD OF THE INVENTION

The present invention provides compositions and methods for increasing the transfer of nucleic acids into cells. In particular, the present invention provides for the use of inhibitors of HDAC6, a cytoplasmic histone deacetylase present in mammalian cells by, for example, small molecules or siRNA treatment, in increasing gene transfer and/or expression in cells in vitro and in vivo for research and gene therapy applications.

BACKGROUND

A primary limitation of gene therapy, specifically non-viral gene therapy, is an inability to achieve high levels of expression. The cell and nuclear membranes as well as the dense meshwork of the cytoplasm all present obstacles to DNA transfer that must be overcome in order for the DNA to reach the nucleus and be transcribed. Much work has been devoted to overcoming the barriers presented by the cellular and nuclear membranes, while what occurs in the cytoplasm is only beginning to be discovered. Previous work has demonstrated that after liposome mediated transfections, a significant amount of DNA remains free in the cytoplasm and does not reach the nucleus, which may contribute to the low levels of expression [1, 2]. Further, the cytoplasmic environment is too densely populated by proteins and cytoskeletal elements for DNA to simply diffuse to the nucleus [3-5]. As such, what is needed are compositions and methods to facilitate high levels of transfection and expression of vector based sequences.

SUMMARY OF THE INVENTION

The present invention provides compositions and methods for increasing the transfer of nucleic acids into cells. In particular, the present invention provides for the use of inhibitors of HDAC6, a cytoplasmic histone deacetylase present in mammalian cells by, for example, small molecules or siRNA treatment, in increasing gene transfer and/or expression in cells in vitro and in vivo for research and gene therapy applications.

In developing embodiments of the present invention, it was determined that while bulk microtubules are disassembled, a class of stabilized microtubules that are posttranslationally modified by acetylation are induced. In separate studies it was observed that plasmids move through the cytoplasm to the nucleus along microtubules using the motor protein dynein. Other studies have shown that acetylated microtubules are better than unmodified microtubules at recruiting and activating the dynein motor. Thus, experiments were performed to determine whether these acetylated microtubules help to increase trafficking of the plasmids to the nucleus. Although the enzyme responsible for acetylation of microtubules has not been identified, the major tubulin deacetylase (HDAC6) has been identified. Thus, experiments were performed to determine if by increasing levels of acetylated microtubules, increases in gene transfer would also be realized. Several methods were therefore employed to inhibit HDAC6, including siRNAs and small molecule inhibitors. It was found that inhibition of HDAC6 increases gene transfer and expression by about 10- to about 100-fold as early as 2 hours post-transfection and at times up to 48 hours post-transfection. While other studies have employed HDAC inhibitors to increase transcription, none have specifically targeted or identified HDAC6 as a molecular target to increase DNA trafficking. As HDAC inhibitors are in clinical trials as anti-tumor agents, it is herein contemplated that administration of these inhibitors to either laboratory in vitro gene transfer or to in vivo gene therapy applications in animals and humans is amenable to ongoing efforts in increasing nucleic acid delivery for gene therapy and research applications.

In some embodiments, the present invention provides a composition for increasing gene transfer into cells (e.g., lung cells) comprising an inhibitor of HDAC6 and a gene transfer reagent. In some embodiments, said gene transfer reagents are lipids, calcium phosphate, microinjection, electroporation, or DEAE/dextran. In some embodiments, an inhibitor is trichostatin A or compound 17b, while in other embodiments an inhibitor is a siRNA to HDAC6. In particular embodiments, the siRNA to HDAC6 is selected from the group consisting of:

| | |
|---|---|
| 5'-GCTTCTAACTGGTCCACTATA-3'; | (SEQ ID NO: 1) |
| 5'-GGATTGGGATGTTCATCATGG-3'; | (SEQ ID NO: 2) |
| 5'-GGACTTTAATACCCAGGATGT-3'; and | (SEQ ID NO: 3) |
| 5'-GCCTTCCTATTGACGTACATG-3'. | (SEQ ID NO: 4) |

In some embodiments, the present invention provides methods for increasing the expression of nucleic acids (e.g., encoding for gene products) in cells comprising providing a gene transfer system, an inhibitor of HDAC6, mammalian cells, and a vector for gene transfer and contacting said cells with said vector and said inhibitor of HDAC6 in the presence of said gene transfer system wherein gene expression from said vector is increased as compared to when an inhibitor is not present. In some embodiments, an inhibitor is a compound, for example, trichostatin A, or a siRNA directed to inhibiting HDAC6 expression. In some embodiments, said gene transfer system is electroporation, lipids, calcium phosphate, or DEAE/dextran. In some embodiments, the cells are in vitro or in vivo.

In some embodiments, the present invention provides a system comprising an inhibitor of HDAC6 and an electroporation system wherein said inhibitor is located within said electroporation system. In some embodiments, the inhibitor is trichostatin A wherein in other embodiments the inhibitor is an siRNA directed to inhibiting HDAC6 expression.

In particular embodiments, the present invention provides methods for transfecting lung cells comprising: contacting lung cells with a gene transfer system and a vector under conditions of cyclic stretch such that gene expression from said vector is increased by employing said conditions of cyclic stretch compared to expression when cyclic stretch is not employed. In further embodiments, the contacting is in vivo in a subject. In some embodiments, the condition of cyclic stretch comprise ventilating the subject. In particular embodiments, cyclic stretch is caused to the lung cells at about 12-24 ml/kg (e.g, 12 ... 15 ... 18 ... 21 ... 24 ml/kg) for a limited time (e.g., 1-5 minutes, 2-5 minutes, 3-4 minutes, about 2 minutes, about 3 minutes, about 4 minutes, etc.) after vector delivery by electroporation. In certain embodiments, the gene transfection levels are sufficient to increase fluid clearance in the lungs.

In certain embodiments, the present invention provides methods for increasing nucleic acid expression in cells comprising: a) providing: i) a gene transfer system; ii) cells, and iii) a vector, b) contacting the cells with the vector under conditions of cyclic stretch in the presence of the gene transfer system such that gene expression from the vector is increased by employing conditions of cyclic stretch compared to expression when cyclic stretch is not employed. In certain embodiments, the cells are lung cells (e.g., in a subject or in a container). In certain embodiments, the contact is done in vitro. In other embodiments, the contacting is done in vivo in a subject. In particular embodiments, the conditions of cyclic stretch comprise providing ventilation at sufficient tidal volumes to a patient to cause cyclic stretch. In certain embodiments, the gene transfer system comprises devices to cause electroporation type transfection, including those useful to perform electroporation in vivo. In certain embodiments, the subject is suffering from: acute lung injury, acute respiratory distress syndrome (ARDS), or neonatal respiratory distress syndrome. In certain embodiments, the vector is a non-viral vector. In some embodiments, the cells are pulmonary epithelial cells.

DEFINITIONS

Figure 1:
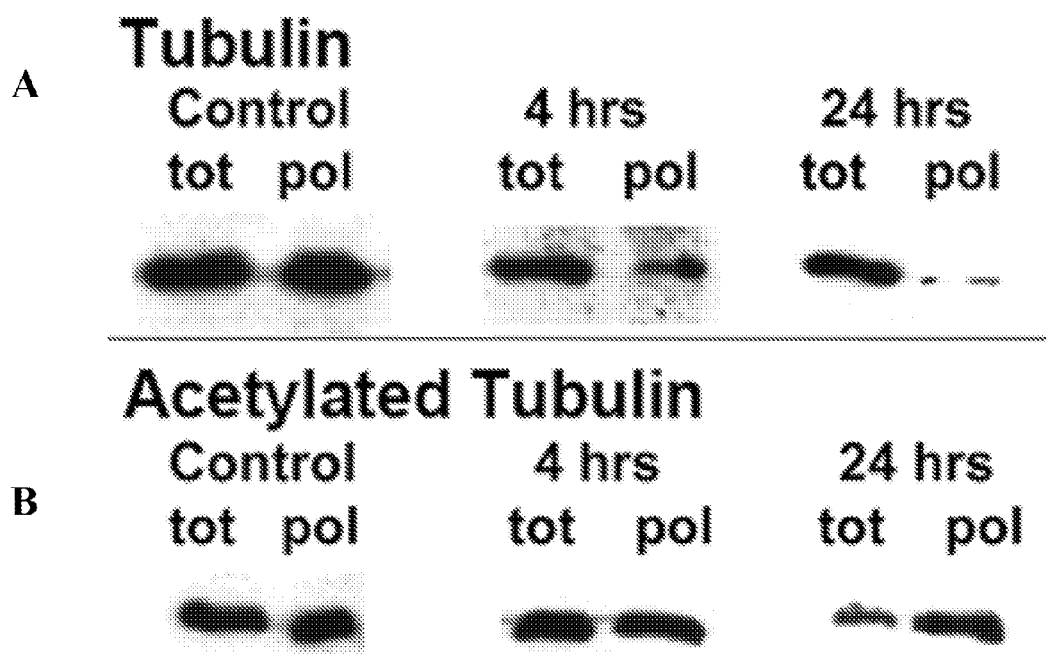
FIG. 1 shows western blots for total and acetylated tubulin under conditions of stretch. As stretch increases out to 24 hours, the amount of polymerized total tubulin (pol) decreases (A), while the amount of polymerized acetylated tubulin (B) remains relatively constant. In both experiments, polymerized tubulin total protein amounts were loaded at twice the level of total tubulin total protein amounts.

The term "gene" refers to a nucleic acid (e.g., DNA or RNA) sequence that comprises coding sequences necessary for the production of a polypeptide or precursor (e.g., a protein of interest). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. During the time the foreign DNA persists in the nucleus it is subject to the regulatory controls that govern the expression of endogenous genes in the chromosomes. The term "transient transfectant" refers to cells that have taken up foreign DNA but have failed to integrate this DNA.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses. Vectors typically encode for a desired gene product, such as a reporter gene (luciferase, green fluorescent protein, etc.), a functional gene, or other gene products as decided by an investigator.

DETAILED DESCRIPTION OF THE INVENTION

Experiments were performed, in developing embodiments of the present invention that provide novel compositions and methods for increasing gene transfer and/or expression to cells. Non-viral gene therapy was contemplated, however it was also important that methods and compositions be widely applied, such that the invention would not be limited to only gene therapy applications, but would also be useful is general and applied research and development endeavors.

In previous experimentation, it was found that cyclic stretch increased exogenous gene expression (Geiger et al., 2006, Gene Ther. 13: 725-731; Taylor et al., 2003, Mol. Ther. 7: 542-549) while decreasing the amount of polymerized tubulin in the transfected cell cultures (Geiger et al., 2006). Many groups have shown that microtubules undergo several types of posttranslational modifications, including detyrosination (Arce et al., 1975, Eur. J. Biochem. 59:145-149), acetylation (L'Hernault & Rosenbaum, 1985, Biochem. 24:473-478), and glutamylation (Edde et al., 1990, Science 247:83-85). Of particular interest was tubulin acetylation, which has been shown to retard microtubules depolymerization due to drug treatments with colcemid (Matsuyama et al., 2002, EMBO J. 21:6820-6831) in a MAP (microtubule associated protein)-dependent fashion. Furthermore, this type of modification has been suggested to increase the association of microtubules with molecular motors, and increase the rate of anterograde transport of kinesin-bound cargo (Reed et al., 2006, Curr. Biol. 16:2166-2172).

In developing embodiments of the present invention, experiments were performed to determine if cyclic-stretch increased the amount or concentration of tubulin acetylation in in vitro cell cultures. Results from such experiments compared, via western blot, the amount of acetylated versus total tubulin in the polymerized pools of lysed cells subjected to up to 24 hours of cyclic stretch. Western blot analysis demonstrated that there was an increase in the concentration of acetylated tubulin in the polymerized tubulin pool (FIG. 1). This result suggested that although cyclic stretch was decreasing the overall amount of polymerized tubulin, it was not affecting the microtubules that were acetylated, as the amount of acetylated signal as measured by western blot did not change with increasing amounts of cyclic stretch. In subsequent experiments, the activity of the microtubule deacetylase, HDAC6, was altered to increase microtubule acetylation in the in vitro test cultures. HDAC6 activity was modified through a variety of methodologies, including drug treatment with general HDAC inhibitors, siRNA knockdown of HDAC6, and specific inhibitors of HDAC6.

Figure 2:
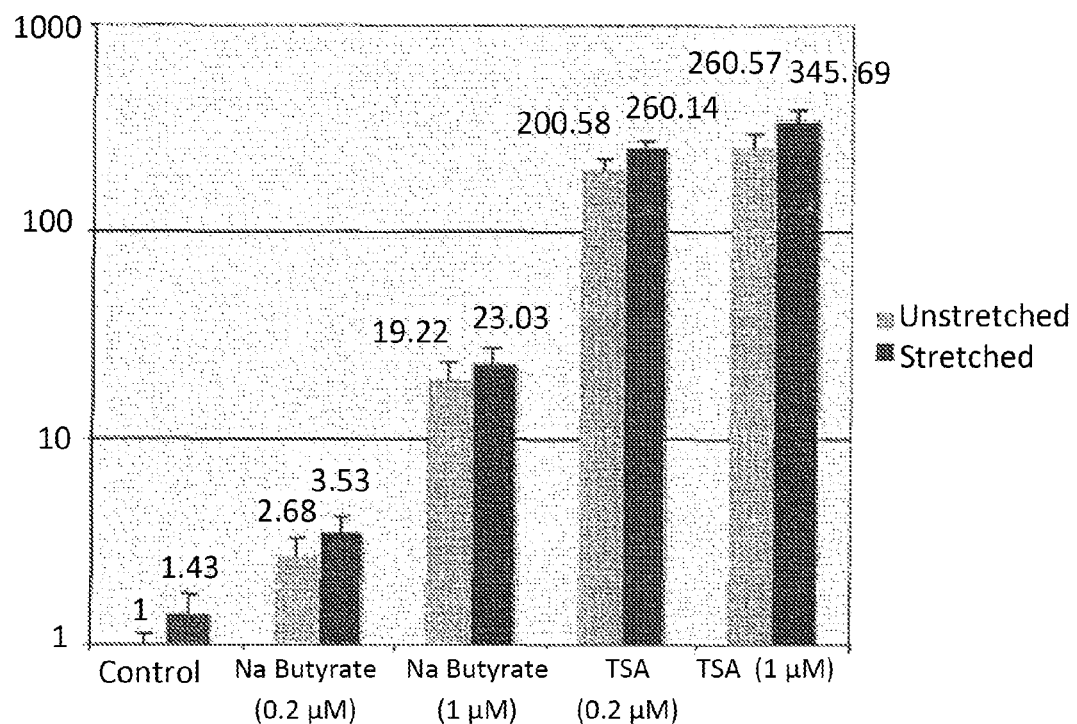
FIG. 2 shows exogenous gene expression for total and acetylated tubulin under drug treatment. Using several broad inhibitors of HDAC activity, it was found that exogenous gene expression increased compared to vehicle controls 24 hours post transfection. A549 cells were transfected using electroporation with 10 pg of a pCMV-LUX-DTS plasmid previously described (Taylor et al., 2003, Mol. Ther. 7:542-549). Cells were harvested and luciferase values measured 24 hours after electroporation and 25 hours after drug treatment.
Figure 3:
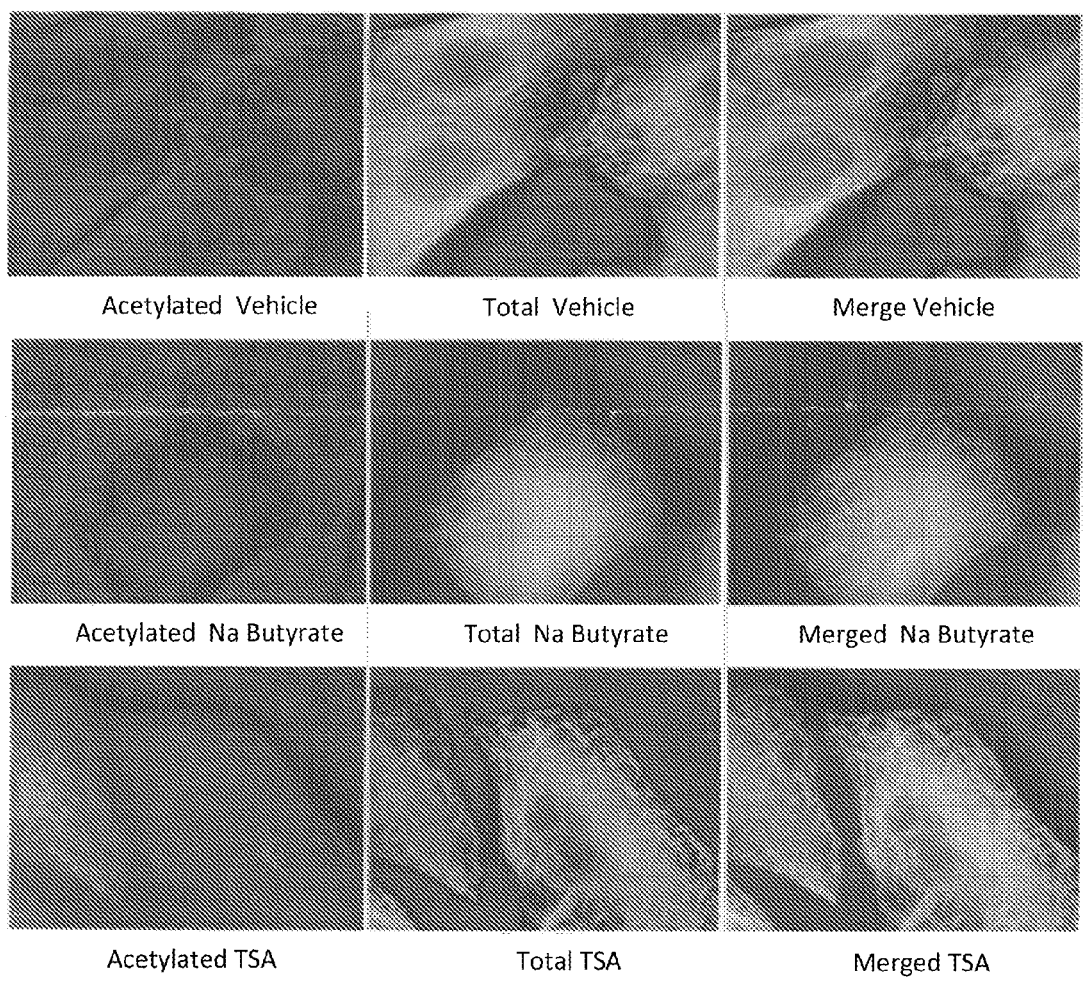
FIG. 3 shows immunofluorescence for total and acetylated tubulin under drug treatment. Using several broad inhibitors of HDAC activity, it was found that the number of acetylated tubulin only increased upon the addition of trichostatin A (TSA, bottom panels), and not with sodium butyrate (Na Butyrate, middle panels).

In developing embodiments of the present invention, the effects of two HDAC inhibitors on cell cultures, sodium butyrate and trichostatin A, was evaluated. Sodium butyrate has been previously shown to be a non-specific HDAC inhibitor that does not inhibit HDAC6. Trichostatin A (TSA) is another non-specific HDAC inhibitor that is known to inhibit HDAC6. These drugs were evaluated such that differentiation between HDAC6 dependant and independent cellular actions was determined. Experiments were performed to determine if either of these drugs had a significant effect on exogenous gene expression. It was observed that TSA caused microtubule acetylation in cell cultures (FIG. 2) and both sodium butyrate and TSA caused significant increases in exogenous gene expression 24 hours after electroporation and 25 hours after the administration of the drugs. It was further observed that the cells treated with TSA, which does inhibit HDAC6 activity, caused nearly a 10-fold higher increase in expression than did sodium butyrate. This result demonstrated that there were observable differences in the ability of these two drugs to increase exogenous gene expression microtubule acetylation. Further experiments were performed to determine whether these drugs caused microtubule acetylation. As seen in FIG. 3, treatment with TSA caused significant microtubule acetylation over treatment controls that were not observed using sodium butyrate.

Figure 4:
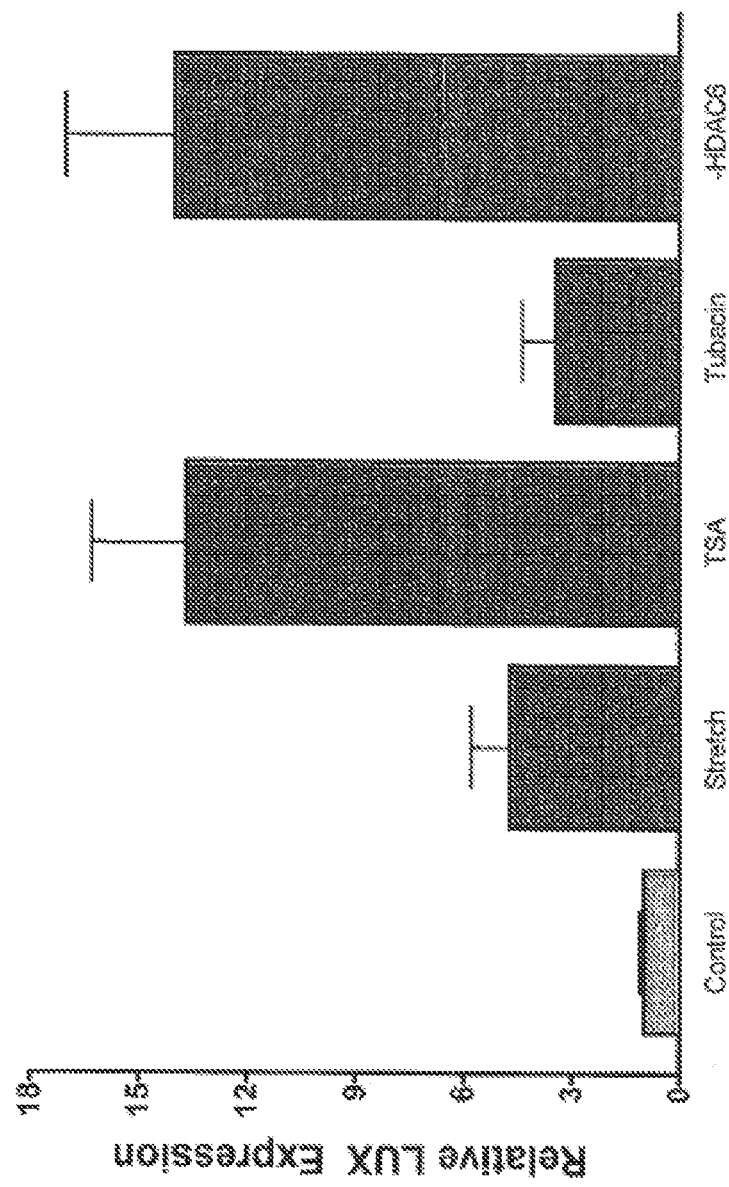
FIG. 4 shows multiple methods of decreasing HDAC6 activity causes increased exogenous gene expression. Several methods of inhibiting HDAC6 activity including cyclic stretch (Stretch), trichostatin A (TSA), a small molecule inhibitor of HDAC6 called Tubacin or knocking down HDAC6 activity with siRNA against HDAC6 (—HDAC6) were used in A549 cell cultures. In each instance, exogenous gene expression as measured by luciferase expression was increased over the appropriate control conditions.

In developing embodiments of the present invention, further experimentation was performed to examine how inhibition of HDAC6 affected gene expression in cell cultures. A variety of methods to specifically inhibit HDAC6 without affecting the other HDAC activity were utilized. Methods utilized include using a specific small-molecule inhibitor of HDAC6 called tubacin (Haggarty et al., 2003, Proc. Natl. Acad. Sci. 100:4389-4394), and using A549 cells that have had HDAC6 expression inhibited by using siRNA (Kovacs et al., 2005, Mol. Cell. 18:601-607; herein incorporated by reference) molecules. As seen in FIG. 4, regardless of the methodology used to decrease the activity of HDAC6, exogenous gene expression is greatly increased over the appropriate controls. As such, embodiments of the present invention may be practiced with any type of HDAC6 inhibitor, preferably HDAC6 specific inhibitors.

In some embodiments, the present invention provides methods for increasing gene transfer (e.g., nucleic acids encoding gene products) and/or expression into cells. In some embodiments, cells are in vitro in cell culture or are in vivo in subjects. In some embodiments, methods for increasing gene transfer and/or expression to cells comprises the inclusion of inhibitors of HDAC6 in transfection and/or gene transfer methods and compositions readily known to those skilled in the art. In some embodiments, methods and compositions comprising inhibitors of HDAC6 for gene transfer increase rates and extent of gene transfer and/or expression to cells.

In some embodiments, gene transfer is to the nucleus of the cell, while in other embodiments gene transfer is directed to the cytoplasm initially. In some embodiments, the compositions and methods of the present invention are used for gene transfer in tissue culture cells in vitro, for example in a laboratory.

In some embodiments, the present invention is utilized in vivo in, for example, gene therapy applications, research applications (e.g., experimental models of diseases, etc.) in humans and non-human animals. In some embodiments, the compositions of the present invention are added as adjuvants to commercially existing compositions for transfection purposes. Such inclusion allows, for example, increased levels of gene transfer and expression above what is observed without the inclusion of compositions of the present invention.

Various gene transfer methods and systems are known in the art for introducing nucleic acid molecules into host cells (including the specific cell type). In some embodiments, microinjection, in which DNA is injected directly into the cytoplasm of cells through fine glass needles is used in conjunction with compositions of the present invention. In other embodiments, DNA is incubated with an inert carbohydrate polymer (dextran) to which a positively charged chemical group (DEAE, for diethylaminoethyl) has been coupled. The DNA sticks to the DEAE-dextran via its negatively charged phosphate groups. These large DNA-containing particles stick in turn to the surfaces of cells, which are thought to take them in by a process known as endocytosis. In another method, cells efficiently take in DNA in the form of a precipitate with calcium phosphate. In electroporation, cells are placed in a solution containing DNA and subjected to a brief electrical pulse that causes holes to open transiently in their membranes. DNA enters through the holes directly into the cytoplasm, bypassing the endocytotic vesicles through which they pass in the DEAE-dextran and calcium phosphate procedures (passage through these vesicles may sometimes destroy or damage DNA). In other embodiments, vector DNA is incorporated into artificial lipid vesicles, liposomes, which fuse with the cell membrane, delivering their contents directly into the cytoplasm. In still further embodiments, DNA is absorbed to the surface of tungsten microprojectiles and fired into cells with a device resembling a shotgun. In particular embodiments, dendrimer based transfection reagents are employed. In other embodiments, polyethylenimine (PEI) transfection reagents are employed. In further embodiments, microinjection or ultrasound methods are employed for transfection.

The present invention is not limited to the gene transfer systems described herein. One skilled in the relevant art recognizes that modifications and additions to the gene transfer systems described herein may be different for different gene transfer applications. Regardless of the system or application however, the incorporation of compositions of the present invention comprising inhibitors of HDAC6 is contemplated to increase gene transfer efficiency in any gene transfer system.

In some embodiments, compositions of present invention are used in conjunction with gene therapy applications to replace a gene whose expression is down-regulated in a cell of interest (e.g., a lung cell). In other embodiments, gene therapy is used to replace a defective copy of a gene of interest. In still further embodiments, gene therapy is used to down-regulate the expression of a gene that is overexpressed (e.g., through the use of antisense or siRNA technologies). Such applications find use in the treatment of disease (e.g., lung disease) characterized by the aberrant expression of a gene or the presence of a defective copy of a gene. Inclusion of compositions of the present invention provide for increased gene transfer for gene therapy applications and treatments.

Alternatively, compositions of the present invention are used in conjunction with gene therapy vectors that are introduced in vivo by lipids in lipofection. Such inclusion of inhibitors of HDAC6 with in vivo lipofection increases the delivery of the associated gene therapy vector. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Felgner et. al., 1987, Proc. Natl. Acad. Sci. USA 84:7413-7417; See also, Mackey, et al., 1988, Proc. Natl. Acad. Sci. USA 85:8027-8031; Ulmer et al., 1993, Science 259:1745-1748). The use of cationic lipids may promote encapsulation of negatively charged nucleic acids, and also promote fusion with negatively charged cell membranes (Felgner and Ringold, 1989, Science 337:387-388). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931), all of which are contemplated for use with compositions of the present invention.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., 1992, J. Biol. Chem., 267: 963-967; Wu and Wu, 1988, J. Biol. Chem., 263:14621-14624; and Williams et al., 1991, Proc. Natl. Acad. Sci. USA 88:2726-2730). Receptor-mediated DNA delivery approaches can also be used (Curiel et al., 1992, Hum. Gene Ther., 3:147-154; and Wu and Wu, 1987, J. Biol. Chem., 262:4429-4432).

In some embodiments, the present invention provides kits for gene transfer to cells in vitro and/or in vivo. Such kits would comprise, for example, one or more inhibitors of HDAC6 (e.g., small molecules, siRNA molecules, drugs, etc.), buffers, reagents, gene transfer compositions (e.g., lipids, calcium chloride, DEAE/Dextran, etc.), instructions, and the like deemed necessary for introducing nucleic acids into cells. Examples of gene transfer methods and systems, as previously described, are useful as components in a kit of the present invention comprising inhibitors of HDAC6.

It has been well established that cells undergo numerous changes resulting from mechanical changes in their environment, a phenomena which has been extensively studied in the lung. Increases in the "stretching" of cells, or changes in the basement membrane surface area of the lung, as seen in ARDS, has been shown to cause decreased endothelial cell barrier function (37A), which is dependent on microtubule disassembly and ERK 1/2 and p38 MAPK activation (38A). Previous studies have shown that physiological levels of cyclic stretch cause significant microtubule reorganization and disassembly (17A).

As shown in Example 2 below, there is a population of microtubules that remains in these stretched cells that is characterized by their post-translational modifications, namely acetylation. Moreover, this Example shows that mild cyclic stretch appears to increase the amount of acetylated microtubules in cultured cells through the inhibition of the cytoplasmic tubulin deacetylase HDAC6. These results are corroborated by in vivo measurements since mice ventilated at low to moderate tidal volumes for 20 minutes showed increased levels of acetylated microtubules in their lungs 48 hours later. This suggests that in vivo, this type of cytoskeletal reorganization is maintained for an extended period of time when compared to the amount of time the exogenous force was applied.

Figure 15:
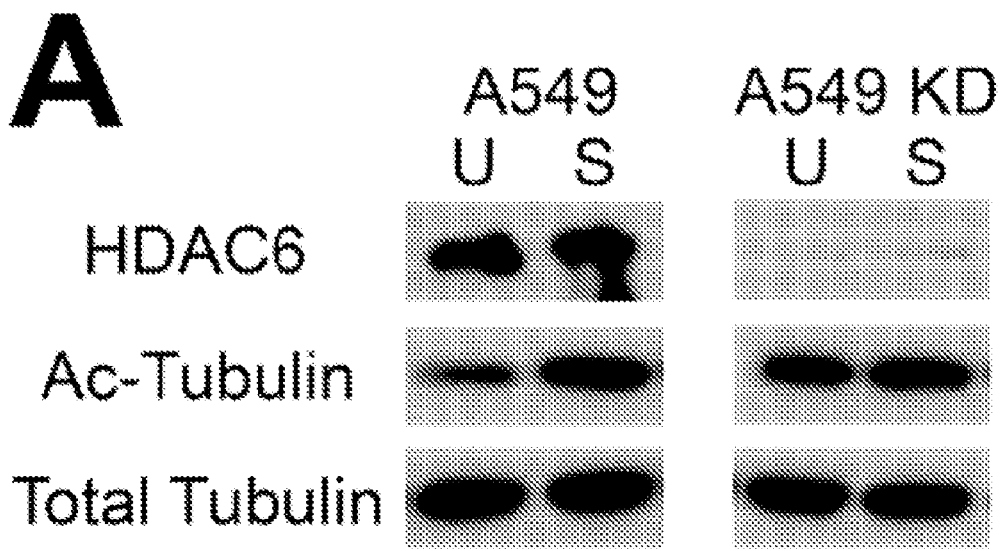
FIG. 15 shows cyclic stretch does not increase acetylated tubulin levels in A549 cells with HDAC6 levels knocked down by siRNA. A549 cells or cells stably transfected to express a siRNA against HDAC6 (A549 KD) were stretched for 24 hours (10% area strain at 0.25 Hz). (A) Western blots of whole cell lysates confirm silencing of HDAC6 in the A549 KD cells and show that acetylated tubulin levels (Ac-Tubulin) were increased in stretched A549 cells (S). However, stretch did not increase acetylated tubulin levels in A549 KD cells with reduced levels of HDAC6. (B) The levels of acetylated relative to total tubulin were quantified by densitometry from Western blots in A (n=3 samples).
Figure 15:
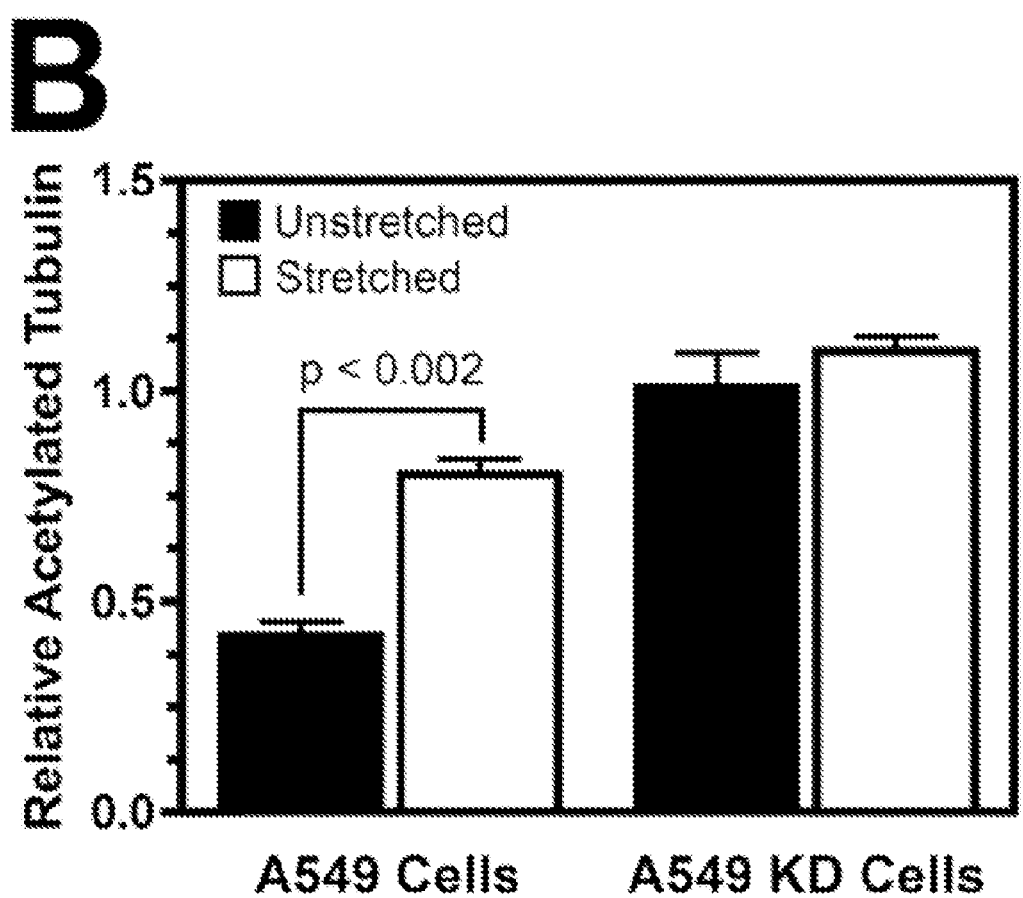
Figure 16:
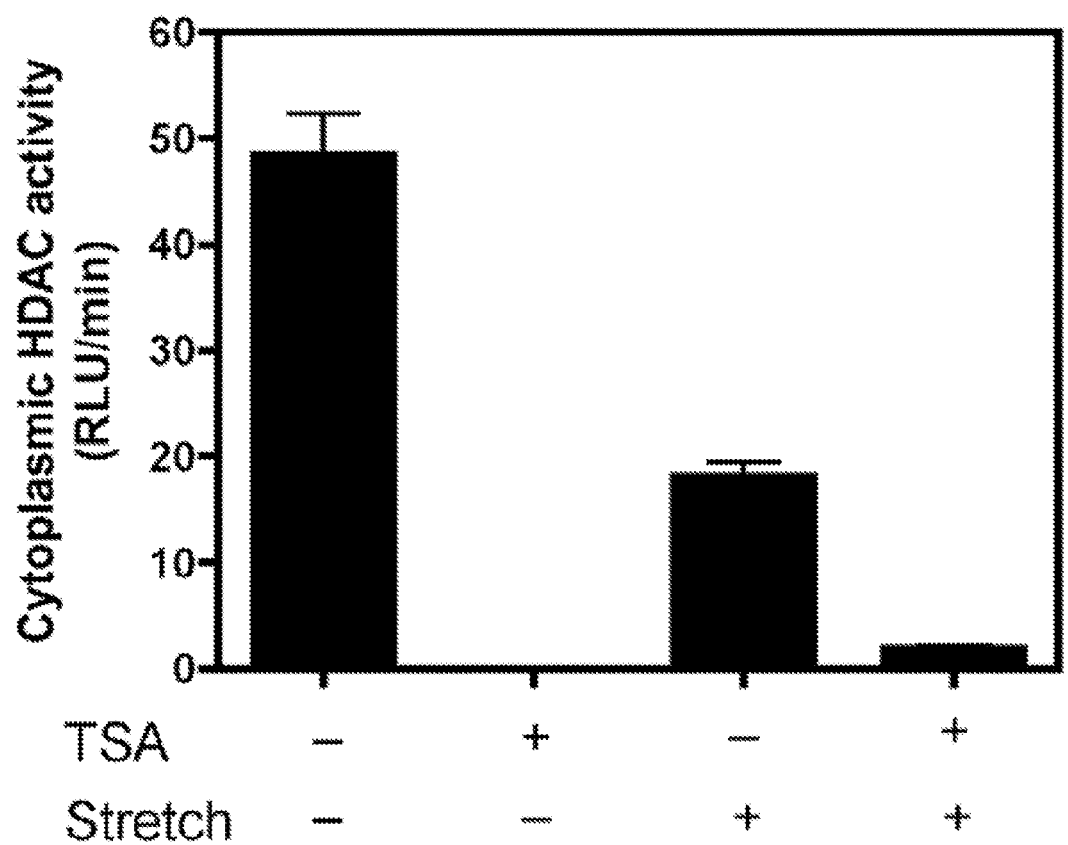
FIG. 16 shows cyclic stretch decreases the activity of cytoplasmic HDACs (HDAC6). A549 cells were stretched for 24 hours (10% area strain at 0.25 Hz). Cytoplasmic extracts were prepared and HDAC activity was measured using a fluorimetric assay as described in Materials and Methods of Example 2. Stretched samples demonstrated a 2.5-fold decrease in cytoplasmic HDAC activity (HDAC6) over unstretched controls. Samples containing trichostatin A (TSA), a known inhibitor of all HDACs, are shown to demonstrate that this activity assay is quenched upon the addition of TSA.
Figure 17:
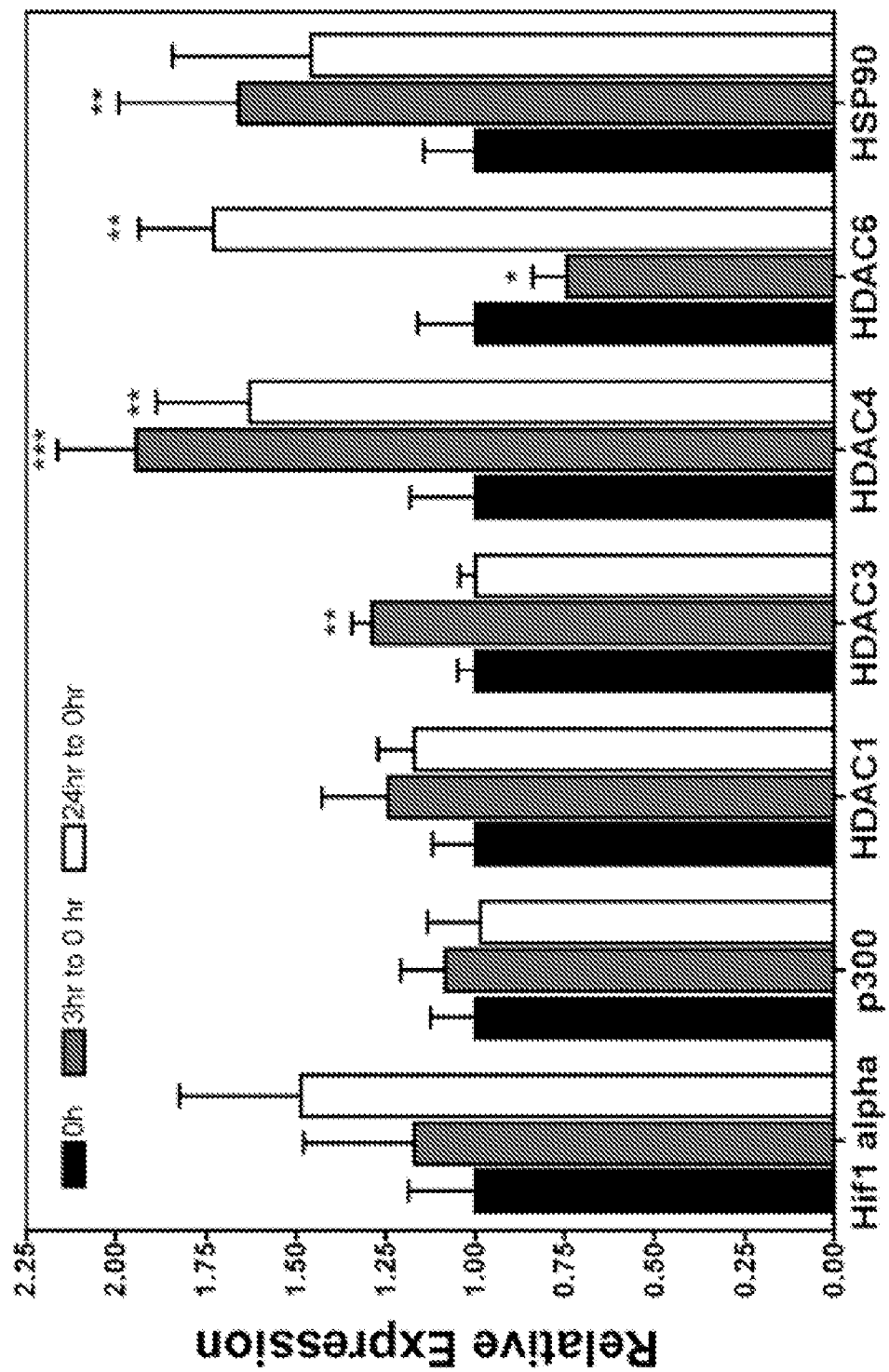
FIG. 17 shows cyclic stretch causes relative changes in mRNA levels as determined by real time PCR. A549 cells were stretched for either 3 or 24 hours (10% S.A., 0.25 Hz., 50% duty cycle), at which time cell lysates were collected for PCR analysis. Relative expression levels were compared to GAPDH. *$p<0.05$, $p<0.01$, *$p<0.001$ versus GAPDH expression level at same time point as determined by a two-tailed Mann-Whitney test.

Although it is still unclear as to whether acetylation is responsible for increased stability or if it is simply a marker for stable microtubules (25A-29A), no methodology short of pharmaceutical inhibitors of HDACs, and in particular HDAC6, have been shown in the literature to cause increased microtubule acetylation. As a result, the function of microtubule acetylation has remained a relative mystery. However, based on the work conducted during the development of the present invention, it would appear that microtubule acetylation preserves cytoskeletal structure in cells undergoing cyclic stretch. Both Western blot and immunofluorescence data demonstrate that polymerized microtubules are highly acetylated in stretched cells. As shown in Example 2, HDAC6 activity is decreased under stretch conditions, however, HDAC6 mRNA levels are not appreciably changed under these same stretch conditions (FIGS. 16 and 17). Similarly, cells treated with HDAC inhibitors (including those specific for only HDAC6), it was observed that similar levels of tubulin acetylation was found in stretched cells (FIG. 15). These results demonstrate that moderate, physiological levels of mechanical stretch can result in significant changes in cellular architecture via modulation of HDAC6.

Work conducted during the development of embodiments of the present invention has demonstrated that electroporation can be used to effectively deliver genes to the lung in vivo with no inflammation or damage to the organ and yield high level of gene expression. Work conducted during the development of embodiments of the present invention also demonstrated that genes can be transferred by electroporation (e.g., transthoracic) to the lungs of mice with existing lung injury and improve clearance of pulmonary edema fluid. As such, in certain embodiments, the present invention provides methods of treating subjects (e.g., human subjects) with the combination of causing cyclic stretch in lung cells (e.g., via ventilation) and electroporation such that therapeutic genes are expressed from a vector in the lung cells (e.g., a non-viral vector). In certain embodiments, the electroporation is transthoracic electroporation, which has been shown to be a safe and effective method for gene transfer to the lungs of mice and rats (see, Machado-Aranda et al., Am J Respir Crit. Care Med, 171: 204-211; and Dean, D. A. 2003. DNA Cell Biol, 22: 797-806; both of which are herein incorporated by reference). It has been shown that this approach does not result in inflammation because electroporation bypasses the TLR9 innate immunity signaling pathway to delivery DNA directly into the cell without activating TLR9 (Zhou et al., Gene Ther, 14: 775-780, 2007, herein incorporated by reference).

In certain embodiments, the present invention provides methods of increasing gene delivery in the lungs of a subject using brief ventilation following (e.g., immediately following) gene delivery by electroporation. In work conducted during the development of embodiments of the present invention, plasmids were delivered to the lungs of mice by electroporation and the mice were ventilated for 5 minutes immediately after gene delivery, causing levels of gene transfer to be increased by 4-5 fold in a statistically significant manner. In certain embodiments, the lungs are normal (non-injured) lungs of a human or an animal. In some embodiments, the lungs are injured lungs of a human or an animal. In particular embodiments, treatment of the lungs with ventilation or other cyclic stretch inducing agent and electroporation causes an improvement in pulmonary edema in injured lungs.

EXAMPLES

Example 1

HDAC 6 Inhibition Results in Increase Transfection

In this Example, after establishing that acetylated microtubules are increased in stretched cells, and are still present in nocodazole treated cells, drug treatments were used to inhibit the tubulin deacetylase, HDAC6, and also HDAC6 knockdown cells, to increase the acetylation of microtubules. It was found that increased acetylation of microtubules increased gene transfer by increasing the trafficking of plasmids toward the nucleus. Finally, other targets of HDAC6 were examined and it was determined that they are not responsible for the observed increase in expression. Taken together, these results indicate that modulation of HDAC6 and the microtubule network can increase the efficiency of gene transfer.

Materials and Methods

Cell Culture, Transfection, and Microinjection

Human adenocarcinoma A549 cells (ATCC, #CCL-185, Rockville, Md.) were grown in DMEM supplemented with 10% fetal bovine serum (FBS). A stable line of A549 cells expressing firefly luciferase was constructed by transfection of cells with plasmid pGL4.14[luc2/Hygro] (Promega, Madison, Wis.) and selection with hygromycin. Colonies were pooled and passaged under selection. HIF-1 and HIF-2 knockdowns were created in A549 cells using retroviral methods with the PT67 packaging cell line (Clontech, Mountain View, Calif.). PT67 cells were transfected with 10 to 15 μg of specific shRNA-expressing or empty plasmids using lipofectin (Invitrogen, Carlsbad, Calif.) according to the manufacturer's protocol. Virus-containing medium was supplemented with 8 μg/ml of polybrene (Sigma, St. Louis, Mo.) for infection. Stable HDAC6 knockdown or stable HDAC6 overexpressing A549 cells were a generous gift from T. P. Yao (Duke University) [28]. For electroporations, cells were grown to confluency in E-well dishes, and rinsed twice in serum- and antibiotic-free media. Five micrograms of plasmids in 500 l of serum and antibiotic-free DMEM were added to each well and one 125 mV square wave electric pulse was applied using a PetriPulser electrode (BTX, San Diego, Calif.). Immediately following electroporation (within 15 seconds), the indicated drug was added to the cells in 1 ml DMEM with 10% fetal bovine serum and antibiotic. Drugs were used at the following final concentrations: 1 μM TSA, 1 mM Sodium Butyrate, 20 mM Nocodazole, 3 mM 17B, 1 mM 17-AAG, and 10 nM Okadaic Acid. When indicated, two hours after electroporation, cells were lysed in Promega lysis buffer and luciferase activity was measured using the Promega Luciferase Assay System, as previously described [29]. All luciferase measurements were normalized to total cell protein and reported as fold-increases in expression over DMSO (vehicle-treated). All experiments were performed in triplicate wells and the experiments were repeated at least three times. For statistical analyses, student's t-tests were used. Cells grown on etched coverslips were microinjected as previously described [30]. At least 100 cells were injected for each condition and experiments were repeated three times.

Plasmids

Plasmid pCMV-lux-DTS expresses luciferase from the CMV immediate early promoter and contains the SV40 DNA nuclear targeting sequence downstream of the reporter gene [31]. All plasmids were purified from *E. coli* using Qiagen Gigaprep kits as described by the manufacturer (Qiagen, Chatsworth, Calif.). Plasmid pDD306, expressing GFP from the CMV promoter and which contains the GeneGrip1 PNA binding site (Gene Therapy Systems, San Diego, Calif.) was labeled with Cy3-labeled PNA as described [30]. Briefly, plasmids were labeled with Cy3-PNA in the manufacturer's labeling buffer at 37° C. for 2 hours followed by isopropanol precipitation to remove unbound Cy3-PNA. Plasmid labeling was verified by agarose gel electrophoresis and fluorescent detection in the absence of ethidium bromide.

Equibiaxial Cyclic Stretch

For all stretch related experiments, A549 cells were plated on Pronectin treated BIOFLEX culture plates. After allowing for attachment for 48-72 h, the cells were stretched using 25 mm BIOFLEX loading stations with a 10% membrane surface area change at 30 cycles per minute and a 50% duty cycle. These parameters are the same as previously reported [14] and the 25 mm loading stations ensure an equibiaxial stretch in the radial and circumferential directions over the width of the loading post.

Microtubule Extraction

Prior to collection, samples were washed once in PBS (37° C.), and stabilized in two 15 minute washes in microtubule stabilization buffer (0.1M PIPES, pH 6.75, 1 mM EGTA, 1 mM MgSO4, 2 M glycerol, protease inhibitors). Cells were then lysed in microtubule lysis buffer (25 mM Tris-HCl, pH 7.4, 0.4 M NaCl and 0.5% SDS).

Western Blots

All extracted samples were mixed with SDS-PAGE sample buffer (112.5 mM Tris-HCl, pH 6.8, 10%-mercaptoethanol, 3.6% SDS, 1.8% glycerol, 0.001% bromophenol blue) such that equal amounts of total protein were loaded for each fraction. The samples were boiled for 3 min and separated by 12% SDS-PAGE gels according to the methods previously described by Lugtenberg [32]. Proteins were transferred to nitrocellulose and probed using anti-acetylated (1:1000, Sigma) or anti-tubulin (1:1000, Sigma) in PBS with 5% fat-free powdered milk. Blots were developed with a chemiluminescence detection kit, and autoradiograms were digitized before densitometry using ImageJ (NIH, Bethesda, Md.). All samples were run in duplicate and were from at least three independent experiments.

Immunofluorescence Imaging.

Figure 5:
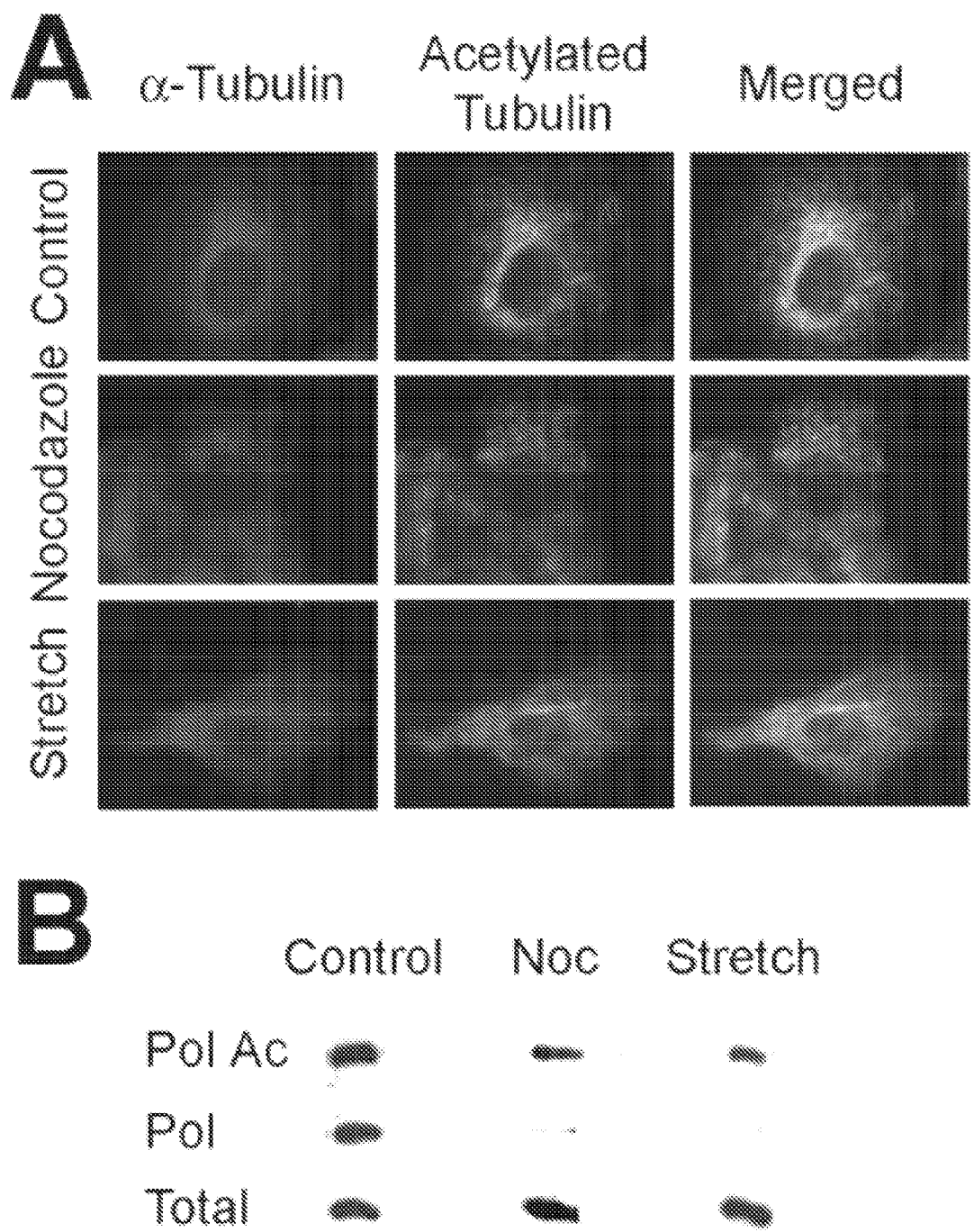
FIG. 5 shows acetylated microtubules are present following nocodazole treatment and are increased following cyclic stretch. A549 cells were grown statically in the absence or presence of 20 mM Nocodazole for 3 hours or stretched (10% change in basement membrane surface area at 30 cycles per minute) for 3 hours in the absence of drug. Cells were either (A) immunostained for total-tubulin and acetylated tubulin, or (B) lysed in microtubule stabilization buffer without Triton X-100 (to obtain total tubulin as a loading control, "Total") or with Triton X-100 to obtain polymerized microtubules ("Pol") and used for Western Blots using antibodies against either-tubulin or acetylated tubulin ("Pol Ac").
Figure 6:
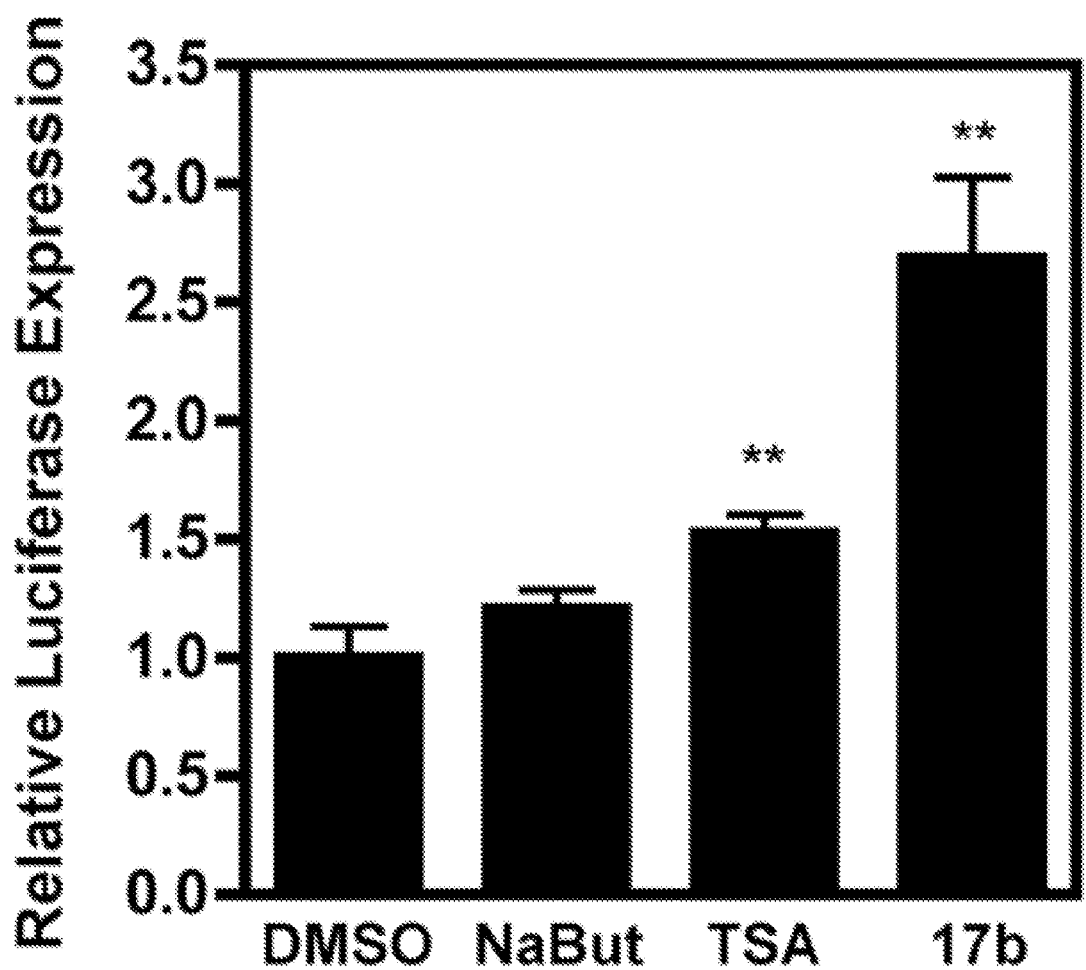
FIG. 6 shows inhibition of HDAC6 increases transfection efficiency. A549 cells were electroporated with pCMV-Lux-DTS and immediately treated with vehicle (DMSO) alone, 1 mM sodium butyrate (NaBut), 1 µM Trichostatin A (TSA, or 3 mM 17b) for three hours after which they were harvested and luciferase activity was measured. Mean luciferase activities±SD (RLU/mg cell protein) were normalized to control transfected cells and experiments were performed in triplicate and repeated at least three times. *p<0.05 by paired student t test.

After all treatment regimes, cells were washed with PBS followed by a 10 minute incubation in fixation/permeabilization buffer (60 mM PIPES, 25 mM HEPES, 10 mM EGTA, 3 mM MgCl2, 0.2% Triton X-100, and 3.7% paraformaldehyde). Cells were then washed in PBS and blocked for 1 hour in PBS containing 1 mg/ml BSA. After blocking, the cells were incubated for 1 hour with the appropriate primary antibody in PBS with 0.1 mg/ml BSA, washed in PBS, and reacted for 30 minutes with Alexa 488 or 555 conjugated secondary antibody (1:200, Molecular Probes, Eugene, Oreg.) in PBS with 0.1% BSA. Following a second set of washes in PBS, the silastic membranes were excised from the culture plates, placed face up on a microscope slide, and covered with a coverslip. All images were acquired in Open-Lab (Improvision, Lexington, Mass.) with a Hamamatsu Orca II-ER camera attached to Leica DRMX-2 upright fluorescent microscope using a 100× oil-immersion objective.
Live Cell Imaging Cells were microinjected on an inverted Leica microscope fitted with a 37° C. acrylic incubation chamber and immediately following microinjection, cells were imaged over time using a Q Imaging Retiga EXi cooled 12-bit camera and the Q-capture Pro suite (Q Imaging, Surrey BC, Canada).
Results
Acetylated Microtubules Remain Intact after Nocodazole Treatment or Cyclic Stretch To determine if acetylated microtubules play a role in trafficking, it was first important to establish their presence. To do this, A549 cells were either stretched or treated with nocodazole. The cells were then harvested and lysed in either microtubule stabilization buffer (total tubulin) or microtubule stabilization buffer containing Triton X-100 (polymerized microtubules only). Equal amounts of sample were then analyzed for tubulin by western blot. It was found that while total levels of tubulin remained constant, as expected, when cells were stretched or exposed to nocodazole, the level of microtubules was greatly diminished. However, acetylated microtubules still remained, suggesting that while there was an overall disruption of the microtubule network, there remained a stable subset of microtubules in the cells (FIG. 5A). These results were confirmed by immunofluorescence of A549 cells for acetylated tubulin (FIG. 5B). Again, after either cyclic stretch for three hours or exposure to nocodazole for three hours, a significant amount of acetylated microtubules remained present in the cells.
HDAC6 Inhibition Results in Increased Gene Expression In order to determine if acetylated microtubules played a role in trafficking, the amount of acetylated microtubules in A549 cells was increased and transfection efficiency of electroporated plasmids was assessed. While acetylation of microtubules occurs by a yet undefined mechanism, deacetylation occurs primarily via histone deacetylase 6 (HDAC6) [15]. Therefore, to increase the amount of acetylated microtubules, HDAC6 was inhibited. Since, the most common inhibitors of HDACs inhibit various HDACs and not HDAC6 specifically, use of these drugs can also inhibit nuclear HDACs, resulting in histone modifications that could ultimately affect expression of transfected plasmids. In order to control for this, the various binding affinities of the different inhibitors was utilized. Sodium butyrate at 1 mM inhibits all HDACs except for HDAC6 [15]. This then serves as a control for plasmid expression levels in the presence of nuclear histone deacetylase inhibition. Trichostatin A at 1 µM, however, inhibits all HDACs including HDAC6 [15]. Thus, the difference between the two should be a reflection of the inhibition of HDAC6, which is to say an increase in acetylated microtubules. Cells were electroporated with a luciferase expressing plasmid and treated with the drugs at the given concentrations and harvested at 3 hours and luciferase expression was determined (FIG. 6). There is a slight but significant increase in the TSA treated cells over both vehicle treated as well as sodium butyrate treated cells, reflecting an increased expression when HDAC6 is inhibited (acetylated microtubules are increased).

Figure 7:
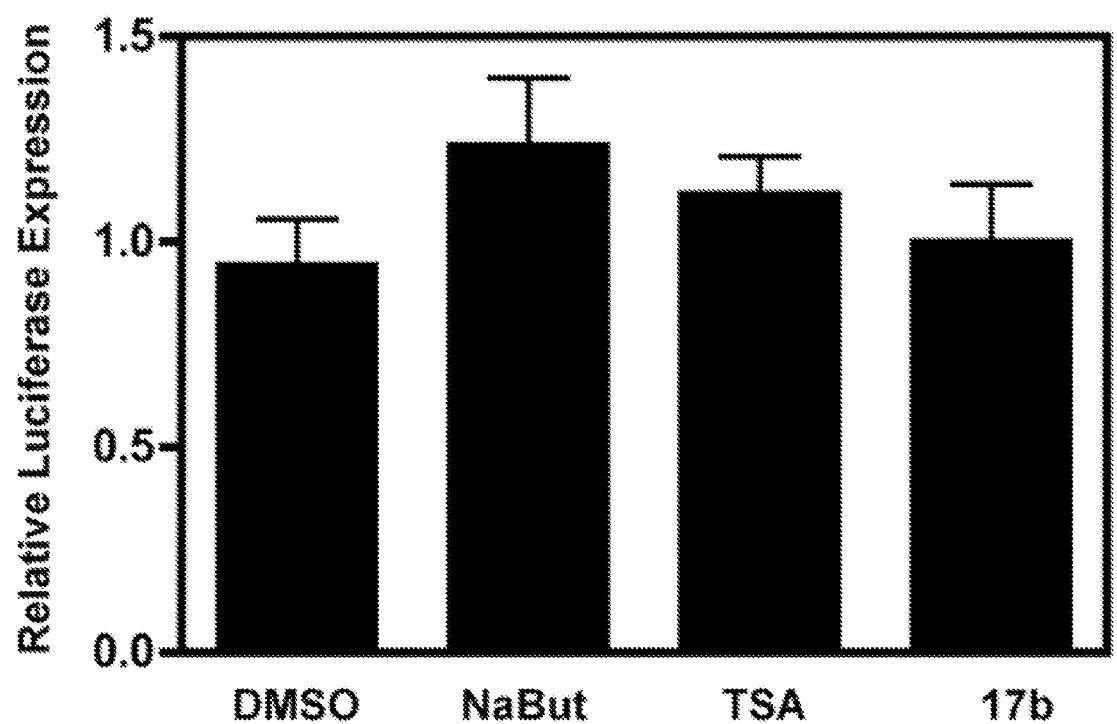
FIG. 7 shows plasmid transcription is not greatly altered by HDAC inhibition. A549 cells stably transfected with a luciferase-expressing plasmid were treated with vehicle (DMSO) alone, 1 mM sodium butyrate (NaBut), 1 µM Trichostatin A (TSA), or 3 mM 17b for three hours after which they were harvested and luciferase activity was measured and compared relative to control (vehicle) cells. Compound 17b is an HDAC6-specific inhibitor that does not inhibit any other known HDAC (ref 16). Mean luciferase activities±SD (RLU/mg cell protein) were normalized to control transfected cells and experiments were performed in triplicate and repeated at least three times.
Figure 8:
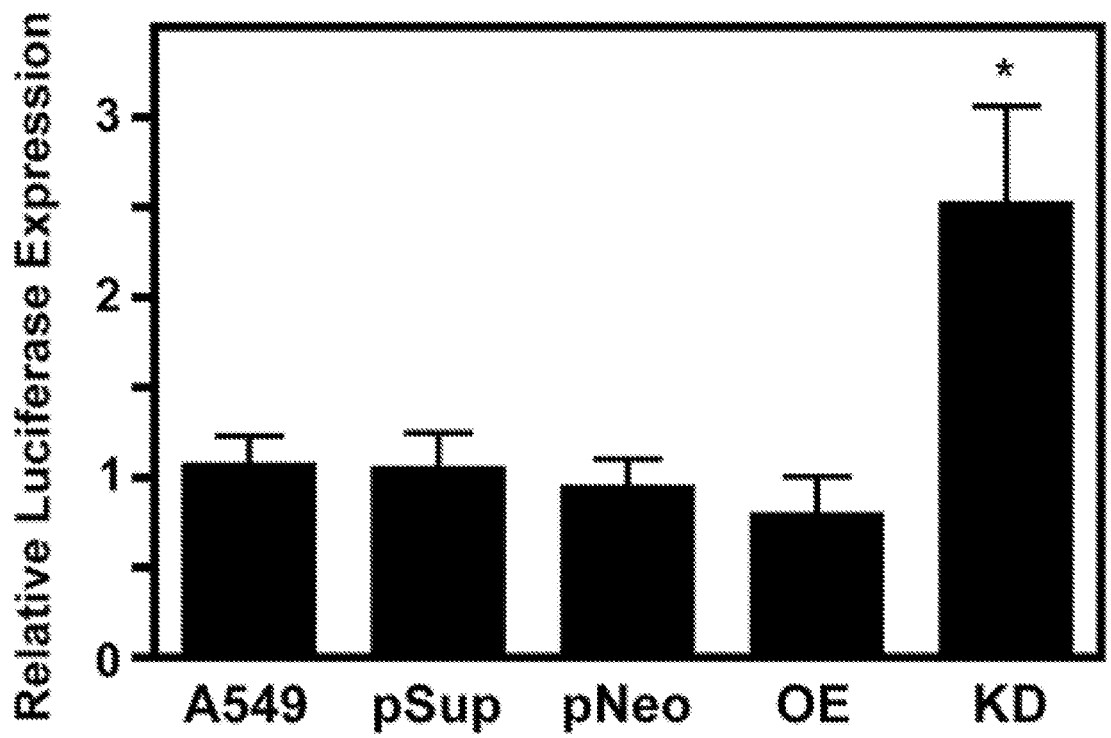
FIG. 8 shows siRNA-induced silencing of HDAC6 increases transfection efficiency. Wild type A549 cells, or A549 cells stably transfected with control plasmids pSuper (pSup) or pNeo, HDAC6 overexpressing plasmid pHDAC6 wt (OE), or an HDAC6 siRNA-expressing plasmid to knock-down expression (1(D)) were electroporated with pCMV-Lux-DTS and 3 hours later luciferase activity was measured. Mean luciferase activities±SD (RLU/mg cell protein) were normalized to transfected wild type A549 cells and experiments were performed in triplicate and repeated at least three times. *p<0.001 by paired student t test.

Although suggestive of a role for HDAC6 inhibition in increasing expression of an electroporated plasmid, a more specific drug was sought to determine the role of HDAC6 inhibition in trafficking Thus, the HDAC6 selective non-hydroxamate, aliphatic thiolate analogue 17b was used as an inhibitor [16]. A549 cells were electroporated with a luciferase expressing plasmid and treated with 17b, followed by harvesting at three hours to determine luciferase expression. Inhibition of HDAC6 again resulted in a significant increase in expression over DMSO (vehicle) treated (FIG. 6).
Inhibition of HDAC6 by 17b Does Not Alter Transcriptional Activity of the Plasmid The non-hydroxamate, aliphatic thiolate analogue 17b has been shown to inhibit HDAC6 specifically [16]. However, it is still possible that treatment with the drug may result in increased transcription and thus the increased expression is not necessarily a reflection of increased or more efficient trafficking. To look at the effects of 17b on transcription directly, a cell line was stably transfected with a luciferase expressing plasmid. These cells were then treated with 17b for three hours, the cells were harvested and expression was determined. Addition of 17b for 3 hours did not show an increase in luciferase expression, suggesting that the drug does not change the transcription of the plasmid (FIG. 7). This suggests that when a plasmid is electroporated and expression is increased, it is due to an in increase in trafficking and not events occurring once the plasmid is in the nucleus.
Knockdown of HDAC6 Results in Increased Trafficking To further address the role of HDAC6 inhibition, a luciferase expressing plasmid was electroporated into stable cell lines, which either over-expressed or knocked down HDAC6 and control cells. Cells were harvested at three hours and expression was determined (FIG. 8). In the control cell lines, pSuper and pNeo, there was no increase in expression observed over untransfected A549 cells. Further, over expression of HDAC6 did not demonstrate a change in expression levels. Knockdown of HDAC6 however resulted in approximate 2.5 fold increase in expression, similar to the increase noted in cells where HDAC6 was knocked down by the chemical compound 17b.

Figure 9:
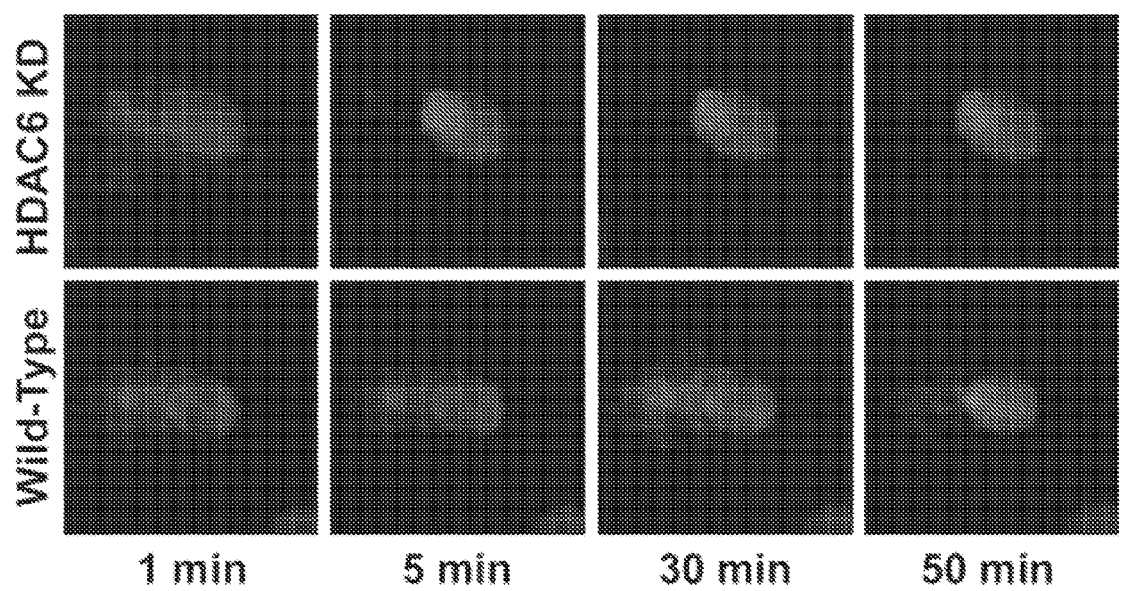
FIG. 9 shows knock-down of HDAC6 increases the rate of cytoplasmic trafficking and nuclear localization of plasmid DNA. Wild type or stably transfected A549 cells expressing siRNA for HDAC6 (HDAC6 KD) were cytoplasmically microinjected with Cy3-PNA-labeled plasmid (0.5 mg/ml). Immediately after injection, cells were imaged for injected DNA at the indicated times. Nuclear DNA was visualized by DAPI staining. At least 100 cells were injected for each condition and experiments were repeated three times. Representative cells are shown in FIG. 9.

To demonstrate directly that silencing of HDAC6 affected DNA cytoplasmic trafficking, plasmids were fluorescently labeled with a Cy3-labeled PNA and microinjected into the cytoplasm of either wild type A549 cells or A549 cells stably expressing siRNA against HDAC6 (FIG. 9). In wild type cells, DNA began to localize to the nucleus within 30 to 50 minutes, as has previously been seen [7, 17]. However, even at 50 minutes postcytoplasmic injection, not all of the DNA has moved to and into the nucleus. By contrast, almost all of the microinjected plasmid has localized to the nucleus of the HDAC6 knockdown cells by 5 minutes after microinjection, confirming that the effects of HDAC6 inhibition are indeed due to cytoplasmic trafficking
Other Targets of HDAC6

Figure 10:
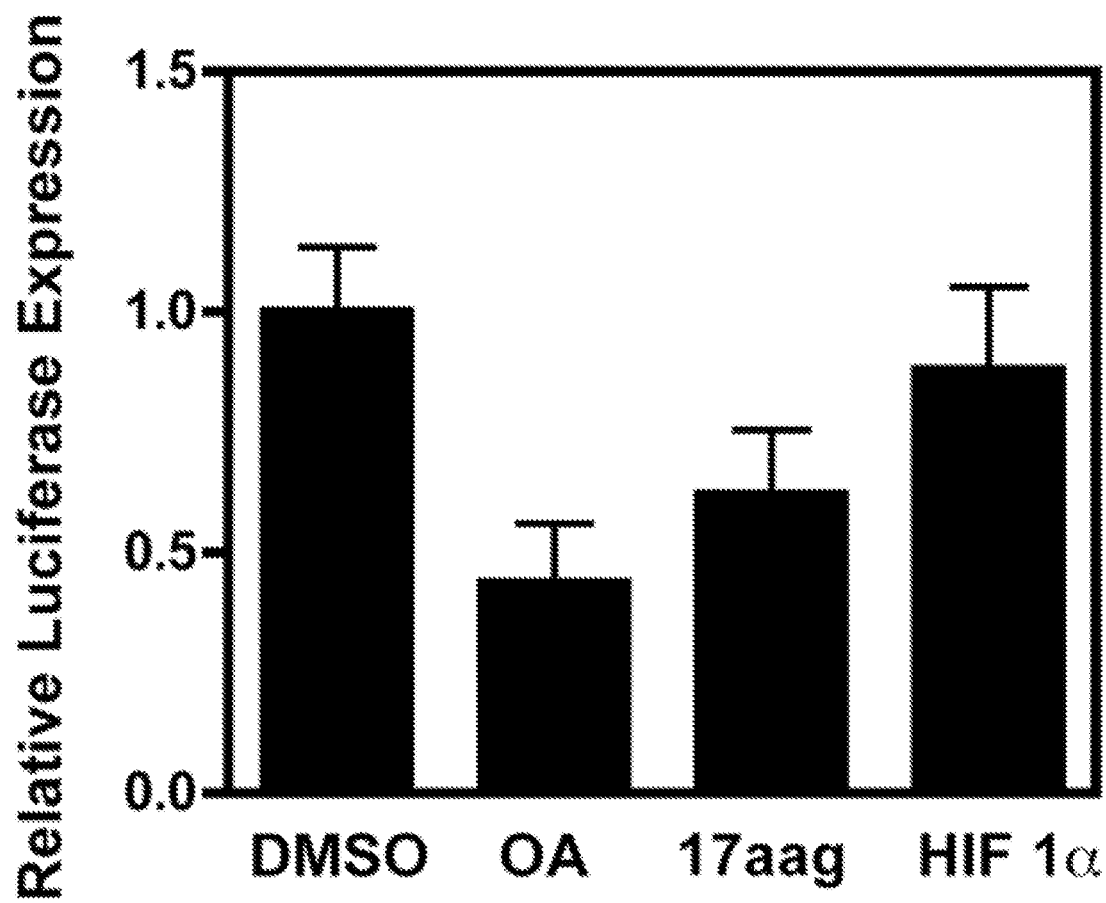
FIG. 10 shows inhibition of non-tubulin HDAC6 targets does not alter DNA trafficking A549 cells or stable A549 transfectants expressing siRNA against HIF-1 were transfected by electroporation with pCMV-Lux-DTS. Transfected wild type A549 cells were immediately treated with vehicle (DMSO), 10 nM okadiac acid (OA), or 1 mM 17-AAG, as indicated. Luciferase expression was determined 3 hours later and mean luciferase activities±SD (RLU/mg cell protein) were normalized to transfected wild type A549 cells. Experiments were performed in triplicate and repeated at least three times.

HDAC6 has been suggested to have roles other than acetylation of microtubules. Therefore, it is possible that the increased expression observed when HDAC6 is inhibited is not mediated by increased trafficking on acetylated microtubules but via another pathway. To address this possibility, various other targets of HDAC6 were examined. To begin with, HDAC6 has also been found to deacetylate heat shock protein-90 (Hsp90) and thereby alter its ability to chaperone proteins [18]. Hence, when HDAC6 is inhibited, Hsp90 becomes hyperacetylated and is unable to chaperone its client proteins. To determine if this alteration in Hsp90 by HDAC6 inhibition is responsible for the increased expression observed, Hsp90 was chemically inhibited via treatment with 17-AAG. A549 cells were treated with 17-AAG immediately following electroporation of a luciferase expressing plasmid, cells were harvested three hours later and luciferase expression was determined (FIG. 10). There was no increase in expression observed when 17-AAG treatment was used. In fact, expression levels were dampened, suggesting that the increase in expression observed with HDAC6 inhibition is not mediated by HSP90.

HDAC6 has also been shown to form a complex with protein phosphatase I (PPI) [19] and that inhibition of HDAC6 disrupts this complex, resulting in an inactive PPI also. To mimic this, PPI was inhibited with okadiac acid. Again, A549 cells were treated with okadiac acid immediately following electroporation with a luciferase expressing plasmid and cells were harvested three hours later to determine luciferase expression (FIG. 10). Treatment with okadiac acid did not result the increase in expression noted when HDAC6 was inhibited, suggesting that the disruption of the PPI-HDAC6 complex is not responsible for the increase in expression observed when HDAC6 is inhibited.

Finally, HDAC6 inhibition has also been shown to inhibit the transcription factor hypoxia inducible factor 1-alpha (HIF-1) [20-23]. To determine if the increase in expression could be attributed to HIF-1 suppression, a stable HIF-1 cell line was created. The knockdown cell line was electroporated with luciferase expressing plasmid and again harvested at the 3 hour time point and found that there was no change in expression between A549 cells and the HIF-1 knockdown cells (FIG. 10).

HDAC6 Overexpression Prevents Stretch Enhanced Gene Transfer

After electroporation, gene transfer is enhanced in cells exposed to cyclic stretch [14]. This Example has shown that after cyclic stretch acetylated microtubules remain (FIG. 5), and further that inhibition of HDAC6 results in an increase in gene transfer that is not attributed to any known interactions of HDAC6 other than an increase in acetylated microtubules.

Figure 11:
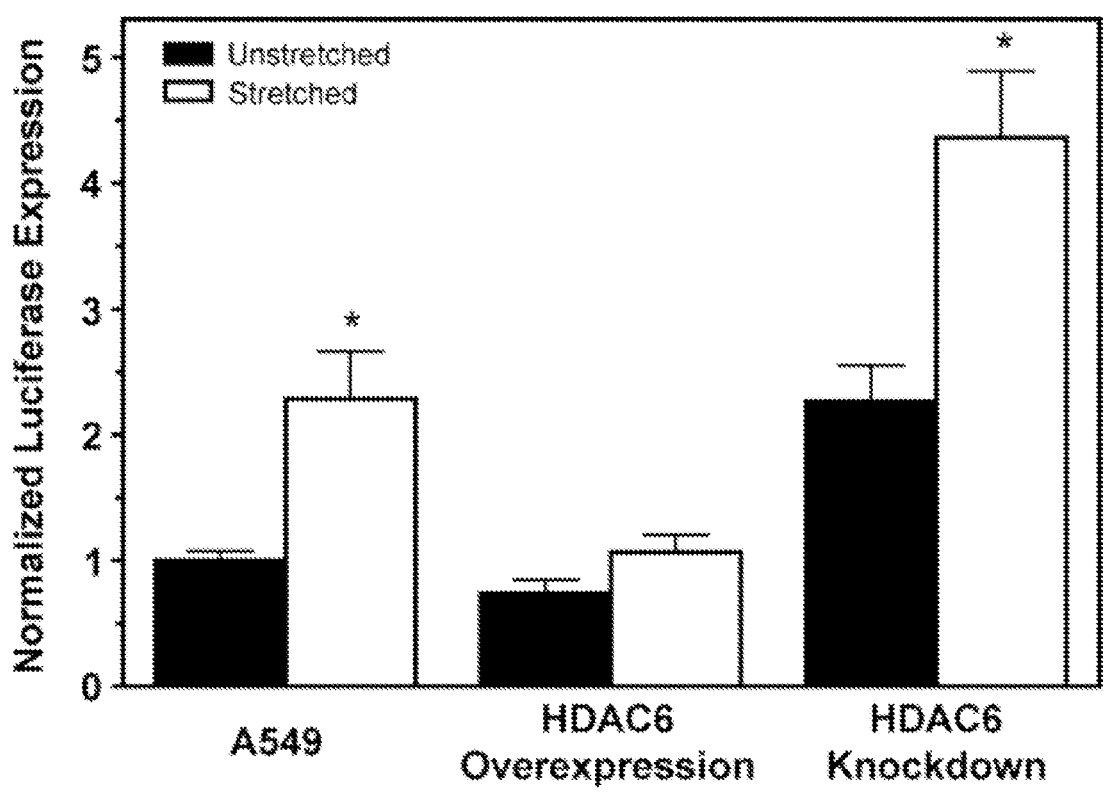
FIG. 11 shows acetylated microtubules are required for stretch enhanced gene expression. A549 cells were electroporated with pCMV-Lux-DTS and immediately exposed to cyclic stretch (10% change in basement membrane area at 30 cycles/min) or grown statically for 3 hours after which cells were harvested and luciferase activity was measured. Mean luciferase activities±SD (RLU/mg cell protein) were normalized to unstretched, transfected wild type A549 cells and experiments were performed in triplicate and repeated at least three times. *, $p<0.01$ compared to unstretched matched cells.

Stable A549 cell lines that overexpressed HDAC6 (few acetylated microtubules) or had knocked-down HDAC6 levels (many acetylated microtubules) were exposed to cyclic stretch immediately following electroporation. After three hours the cells were harvested and luciferase activity was determined. In the overexpressing cell line, where very few acetylated microtubules are present, cyclic stretch did not induce the enhancement normally found when cells are stretched (FIG. 11). However, when HDAC6 was knocked down and more acetylated microtubules are present, the increase (about 2 fold) was seen in stretched cells.

Example 2

Tubulin Acetylation and HDAC6 Activity in the Lung Under Cyclic Load

This Example investigates the relationship between acetylated microtubules and cyclic stretch. This Examples demonstrates that cyclic stretch, at parameters that mimic physiological respiration, increases the amount of acetylated microtubules both in vitro as well as in vivo. This Examples demonstrates that mechanical stimulation can alter tubulin post-translational modifications both in vitro as well as in vivo.

Materials and Methods

Cell Culture. All experiments, except where noted, were conducted on A549 cells, (ATCC, Manassas, Va.) a human lung adenocarcinoma cell line. Stably transfected A549 cells expressing siRNA against HDAC6 were a generous gift from T. P. Yao (Duke University) (27A) and were developed using a retrovirus system expressing an RNAi for HDAC6 causing a significant decrease in HDAC6 levels (33A). Cells were grown in high glucose DMEM supplemented with 10% fetal bovine serum, kanamyacin, and antibiotic/antimycotic solution (Invitrogen, Carlsbad, Calif.). Cells were passaged every three to five days and maintained at 37° C. with 5% CO2. All extractions, washes, fixations and incubations were conducted with buffers warmed to 37° C. unless otherwise noted.

Equibiaxial Cyclic Stretch. For all stretch related experiments, A549 cells were plated on Pronectin treated BIOFLEX culture plates as previously described (17A). Cells were stretched using 25 mm BIOFLEX loading stations with a 10% membrane surface area change at 15 cycles per minute and a 50% duty cycle, unless otherwise noted.

Protein extraction and quantitation. Protein extracts for tubulin that were separated into total tubulin and polymerized tubulin pools were prepared and stored as previously described (34) after a single wash in PBS. Briefly, two 15 minute incubations with microtubule stabilization buffer (MTSB; 0.1 M PIPES, pH 6.75, 1 mM EGTA, 1 mM MgSO4, 2 M glycerol, and protease inhibitors) with or without 0.1% Triton X-100 separated cells into pools containing both polymerized and depolymerized tubulin (those washed in MTSB lacking Triton X-100) and pools containing only polymerized tubulin (MTSB with Triton X-100). The cells were then incubated in lysis buffer (25 mM Tris-HCl, pH 7.4, 0.4 M NaCl, 0.5% SDS) for 5 min before scraping. Cell lysates were boiled for 3 min, centrifuged at 12,000 g for 2 min, and the resulting supernatant was transferred to a new tube. Beta-mercaptoethanol was added to 0.1% of the total volume, and the lysates were then boiled for an additional 3 min and stored at −70° C. Protein extracts from murine lungs were made from snap frozen samples that were pulverized using a BioPulverizer (Biospec Products, Bartlesville, O K). Powdered tissue was suspended in 750 µl of lysis buffer (Promega Corporation, Madison, Wis.), thawed and vortexed. Three rounds of freeze/thaw cycles were done in liquid nitrogen and a room temperature water bath. Supernatant was separated from debris by centrifugation, and 10-12 µg of total protein was added to SDS sample buffer for western blot. For tubulin extracts that were not separated, cells were lysed in SDS-PAGE sample buffer (112.5 mM Tris-HCl, pH 6.8, β-mercaptoethanol, 3.6% SDS, 1.8% glycerol, 0.001% bromophenol blue) and stored at −20° C. Following separation by SDS-PAGE, proteins were transferred to nitrocellulose and probed using anti α-tubulin (1:1000, Sigma, Catalog #T-9026) or anti-acetylated tubulin (1:2000, Sigma, Catalog #T-6793) antibodies in PBS with 5% fat-free powdered milk. All samples were run in duplicate and were from at least 3 independent experiments.

Immunofluorescence Imaging. After all treatment regimes, cells were washed with PBS followed by a 10 minute incubation in a 1× fixation/permeabilization buffer (60 mM PIPES, 25 mM HEPES, 10 mM EGTA, 3 mM MgCl2, 0.2% Triton X-100, and 3.7% paraformaldehyde). Cells were then washed in PBS and blocked for 1 hour in PBS containing 1 mg/mL BSA. After blocking, the cells were incubated for 1 hour with the appropriate primary antibody in PBS with 1 mg/mL BSA, washed in PBS, and reacted for 30 minutes with Alexa 488 or Alexa 555 conjugated secondary antibody (1:200, Molecular Probes, Eugene, Oreg.) in PBS with 0.1% BSA. Following a second set of washes in PBS, the silastic membranes were excised from the culture plates, placed face up on a microscope slide, and covered with a coverslip. All images were acquired in OpenLab (Improvision, Lexington, Mass.) with a Hamamatsu Orca II-ER camera attached to Leica DRMX-2 inverted fluorescent microscope using a 100× oil immersion objective.

Animal Ventilation. Female Balb/C mice (18-22 g) were anesthetized with an intraperitoneal injection of sodium pentobarbital (50 mg/kg body weight) and a tracheostomy was performed using a shortened 20 gauge angiocath. Two ventilation protocols were used: one to investigate persistence of cytoskeletal changes following short periods of ventilation and recovery and one to look at immediate cytoskeletal changes following longer periods of ventilation that mirror times seen to induce changes in acetylated tubulin levels in cultured cells. In the first, mice were mechanically ventilated through the angiocath with a Harvard Small Animal Ventilator (Model 683) at tidal volumes between 10 to 40 ml/kg body weight (20-80% TLC; (35)) for 20 minutes. After ventilation, the animals were allowed to recover and were returned to the vivarium. Forty eight hours later the animals were euthanized by a sodium pentobarbital overdose. The lungs were removed and portions were formalin-fixed for paraffin embedding or snap frozen in liquid nitrogen for preparation of lung lysates. In the second ventilation strategy, the anesthetized animals were connected to the ventilator (Flexivent; SCIREQ Scientific Respiratory Equipment, Inc.; Montreal, Canada) through the angiocath and pancuronium (0.25 mg, i.p.) was administered. The animal was ventilated at a tidal volume of 12 ml/kg with a respiratory rate of 150 for 10 minutes after which baseline measurements of lung mechanics were made using the flexivent protocols. The tidal volume was then increased to 20, 30, 40 or 50 ml/kg and the respiratory rate adjusted to maintain the minute ventilation at 3.5 ml/min. This ventilator strategy was continued for 2 hours except for measurements of lung mechanics using the Flexivent protocols every 30 minutes (approximately 3 minutes per measurement). An additional dose of pentobarbital (80 mg/kg, i.p) was administered after 1 hour and an additional dose of pancuronium was administered if spontaneous movement was noticed. At the end of 2 hours a thoracotomy was performed with removal of the heart and lungs en bloc and processed as above. All experiments were conducted in accordance with institutional guidelines in compliance with the recommendations of the Guide for Care and Use of Laboratory Animals.

Immunohistochemistry. Paraffin embedded mouse lungs were sectioned at 6-micron thickness. Sections were dried, deparaffinized and hydrated into 1×PBS and probed for either acetylated- or total-alpha-tubulin using the M.O.M. kit from Vector Labs (Burlinghame, Calif.) following the manufacturer's directions. Primary antibodies were used at a 1:200 dilution. The secondary antibody was a 1:250 dilution of the M.O.M. biotinylated anti-mouse IgG. Detection and visualization was with Vector Labs Vectastain ABC reagent and DAB substrate solution. Sections were counterstained in hematoxylin.

RNA extraction and real-time quantitative PCR. Total RNA was extracted from stretched cells using QIAshredder and RNeasy kits (Qiagen, Chatworth, Calif.). Extracted RNA was converted to cDNA by performing reverse transcription using 1 ug total RNA with MuLV reverse transcriptase (Applied Biosystems, Foster City, Calif.). Quantitative PCR was performed in a 20 ul reaction volume, using the DyNAmo SYBR Green qPCR Kit as described by the manufacturer (Finnzymes, Espoo, Finland) with an Opticon 2 DNA Engine (MJ Research, Watertown, Mass.) Annealing temperatures were optimized for each set of primers. The threshold was set manually. A melting curve analysis was preformed to ensure reaction specificity. Results were normalized to GAPDH and expressed relative to unstretched data.

HDAC6 Activity measurements. Cytoplasmic lysates were prepared as previously described to separate HDAC6 from nuclear HDAC activity (36). Cells were then probed for HDAC activity using a fluorescent HDAC activity kit (BioMol International LP, Plymouth Meeting, Pa.). At various times during the development of the assay, the reagents were quenched, allowing for a determination of the relative activity of the cytoplasmic HDACs.

Statistical Analysis. All statistical analysis was performed with Prism software (GraphPad Software, San Diego, Calif.), using the Mann-Whitey Wilcoxon test for paired, non-parametric samples. Statistically significant results were denoted at a p value of less than or equal to 0.05.

Results

Stretch Increases Acetylated Tubulin in Cultured Cells.

Figure 12:
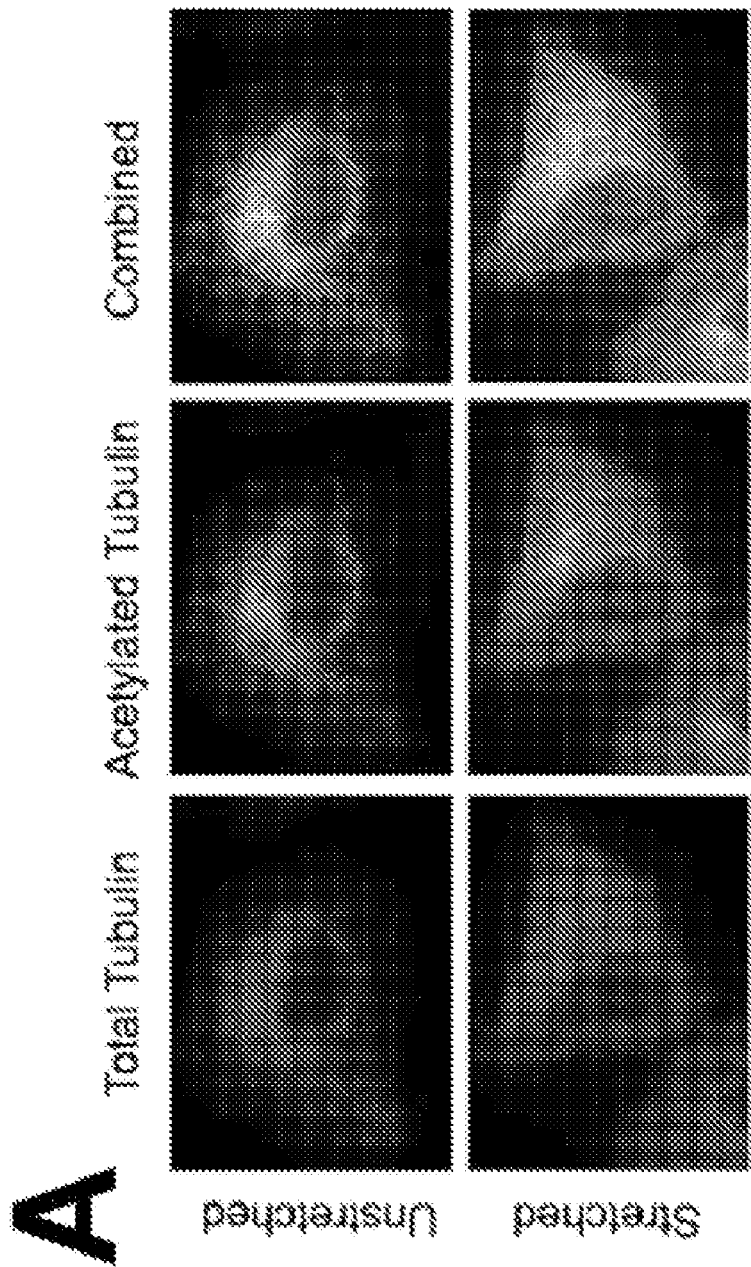
FIG. 12 shows that cyclic stretch alters microtubule network and increases acetylated tubulin in a time dependent fashion. A549 cells were stretched (10% area strain at 0.25 Hz) or grown under static conditions for up to 24 hours. (A) After 24 hours, A549 cells were fixed and visualized via immunofluorescence microscopy. Antibodies against α-tubulin or acetylated tubulin were used to visualize the microtubule network. (B) A549 cells were harvested at the indicated times (n=6). Cell extracts were prepared and the relative levels of acetylated (Ac) and total tubulin was determined by Western blotting. Tubulin levels were normalized to time 0 (i.e., unstretched cells). Densitomitry measurements demonstrate an increase in acetylated tubulin with stretch in whole cell lysates that is not seen in cells in static culture across multiple experiments. (C) Representative Western blot comparing acetylated and nonacetylated polymeric (P) or total (T) tubulin from whole-cell lysates of cells stretched for the indicated times. Tubulin pools were separated into polymeric fractions to emphasize the significant changes seen in the composition of the microtubule (polymerized tubulin) pool with stretch. *$p<0.05$ versus unstretched total tubulin levels at time=0.25 h as determined by a two-tailed Mann-Whitney test.
Figure 12:
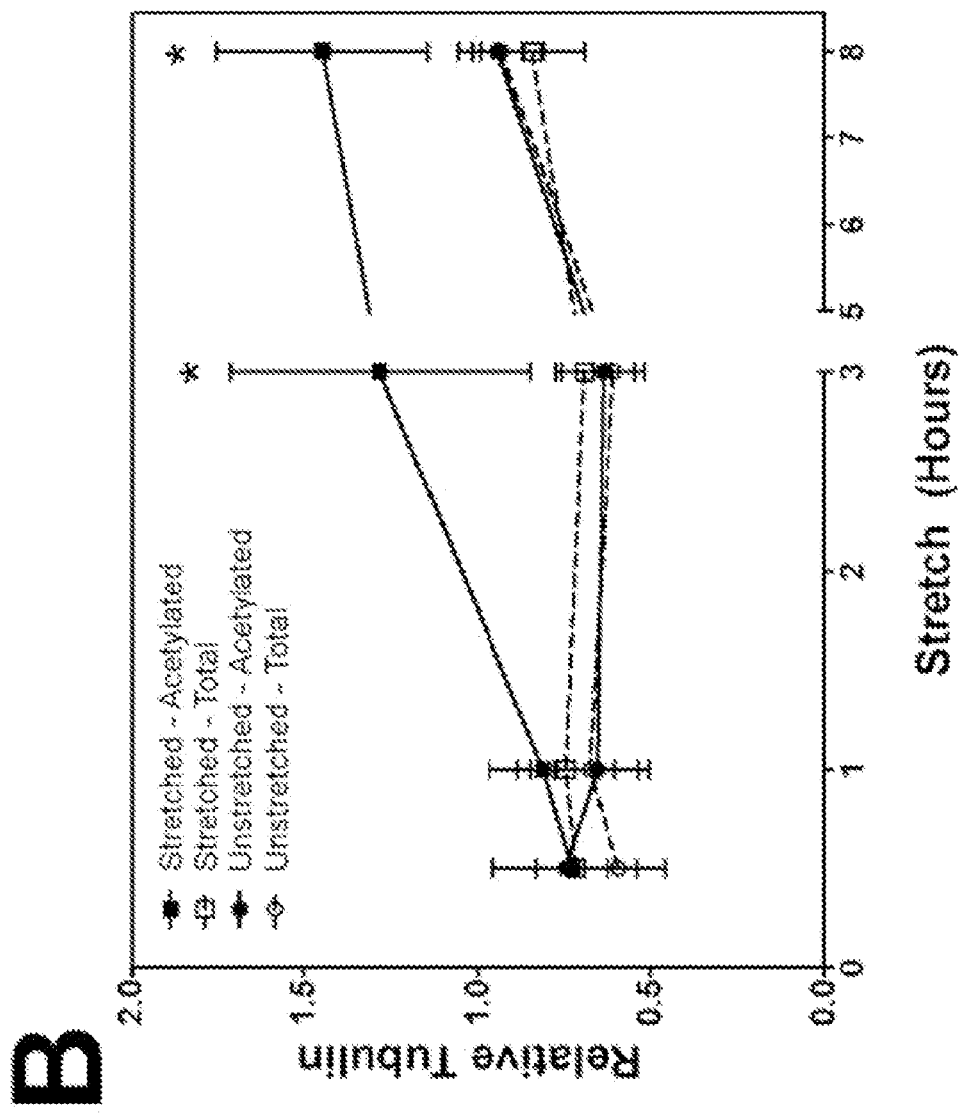
Figure 12:
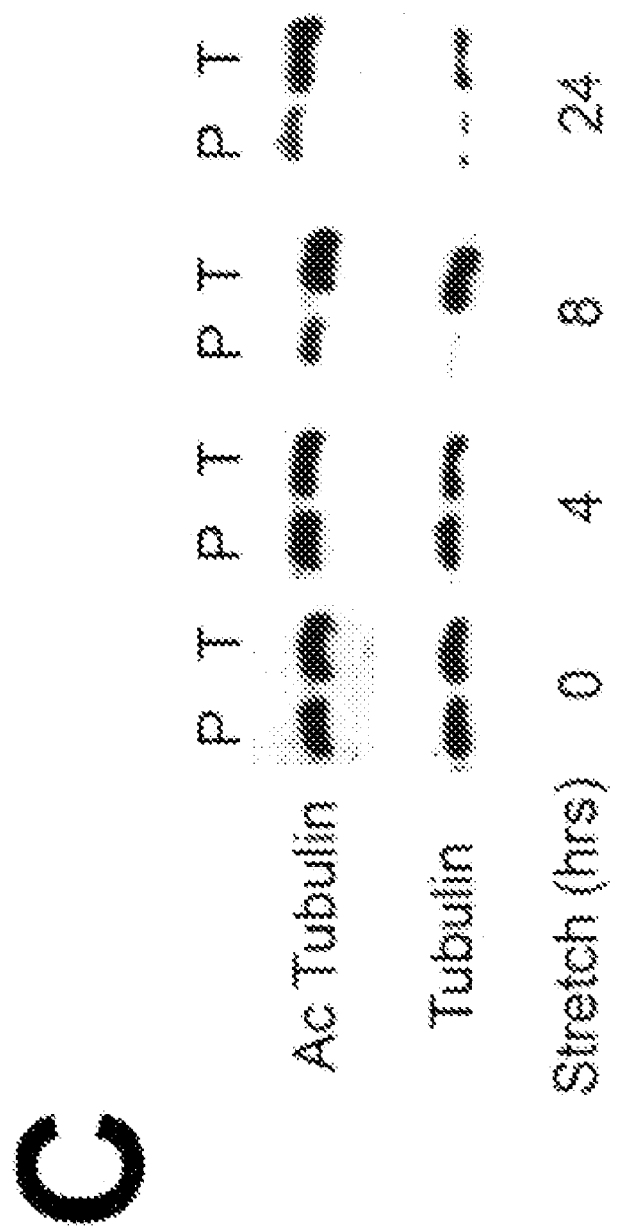

Previous work demonstrated that cyclic stretch caused reorganization of the microtubule network, including a significant reduction in the amount of polymerized tubulin (17A). What was not understood was why some microtubules depolymerized under mechanical loading while others did not. To address this, A549 cells were grown under static conditions of stretch for 24 hours at 0.25 Hz (15 cycles/min) to give a 10% change in basement membrane surface area (SA). When stretched cells were stained for acetylated tubulin, there was an increase in the amount of acetylated tubulin when compared to unstretched controls as demonstrated both by immunofluorescence microscopy (FIG. 12A) as well as western blot analysis (FIG. 12B). As was previously described (17A), stretch resulted in a decrease in the number of microtubules, and those that did remain appeared significantly thickened when compared to unstretched controls. What had not been previously described was the acetylation state of these microtubules, and FIG. 12A demonstrates that almost every visualized microtubule in the stretched cells stained for acetylated tubulin. To further investigate this, cells were grown statically or stretched (10% SA, 0.25 Hz) for shorter durations to determine the timing of these effects. Protein levels were examined at multiple time points by western blot analysis, examining both total cell lysates (FIG. 12B) as well as fractionated cell lysates separating polymerized tubulin from non-polymerized tubulin (FIG. 12C). When the amounts of tubulin were measured relative to time 0, there was a statistically significant increase in the amount of acetylated tubulin under stretch conditions over time versus unstretched controls (FIG. 12B). On average, whole cell lysates from stretched cells showed a 44% increase in acetylated tubulin compared to time matched unstretched controls, ranging from a 12% increase within 30 minutes of stretching to a 71% increase at 3 hours of stretch. By separating total from polymerized tubulin (i.e., microtubules), the absolute decrease in polymerized microtubules in response to cyclic stretch becomes evident as does the relative increase in the amounts of acetylated microtubules compared to total tubulin (FIG. 12C). To ensure that equal loading of total protein occurred, total tubulin values were also measured for both stretch and unstretched cells, and they remained constant throughout the experiment. Taken together, these results demonstrate that mild cyclic stretch increases the levels of acetylated microtubules.

Stretch Increases Acetylated Tubulin In Vivo

Figure 13:
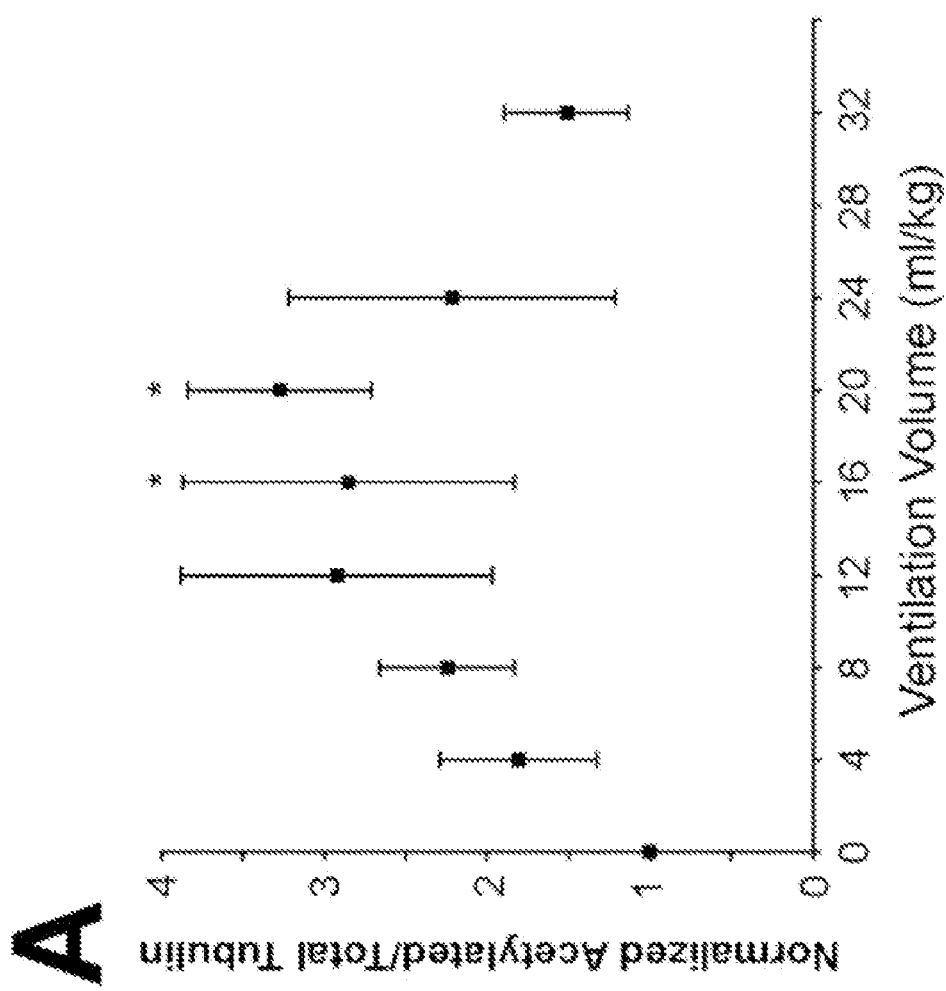
FIG. 13 shows cyclic stretch increases acetylated tubulin in a time and magnitude dependent fashion. Female Balb/c mice (18-22 g) were anesthetized and ventilated at the indicated tidal volumes and the respiratory rate adjusted to maintain the minute ventilation at 3.5 ml/min for 20 minutes (n=4 per condition). The animals were allowed to recover and two days later, total lung lysates were prepared and analyzed for total and acetylated tubulin by Western blot. (A) The ratio of acetylated to total tubulin was normalized to unventilated animals to show that levels of acetylated tubulin increases with ventilation up to 12 to 24 ml/kg and then decreases at higher tidal volumes. (B) Representative Western blot data from non-ventilated (N) and ventilated animals. (C) Representative immunohistochemistry for acetylated tubuiln (blue) of paraffin thin sections from non-ventilated (NV) and ventilated animals. Sections were conunterstained with eosin. *$p<0.05$ versus non-ventilated controls as determined by a two-tailed Mann-Whitney test.
Figure 13:
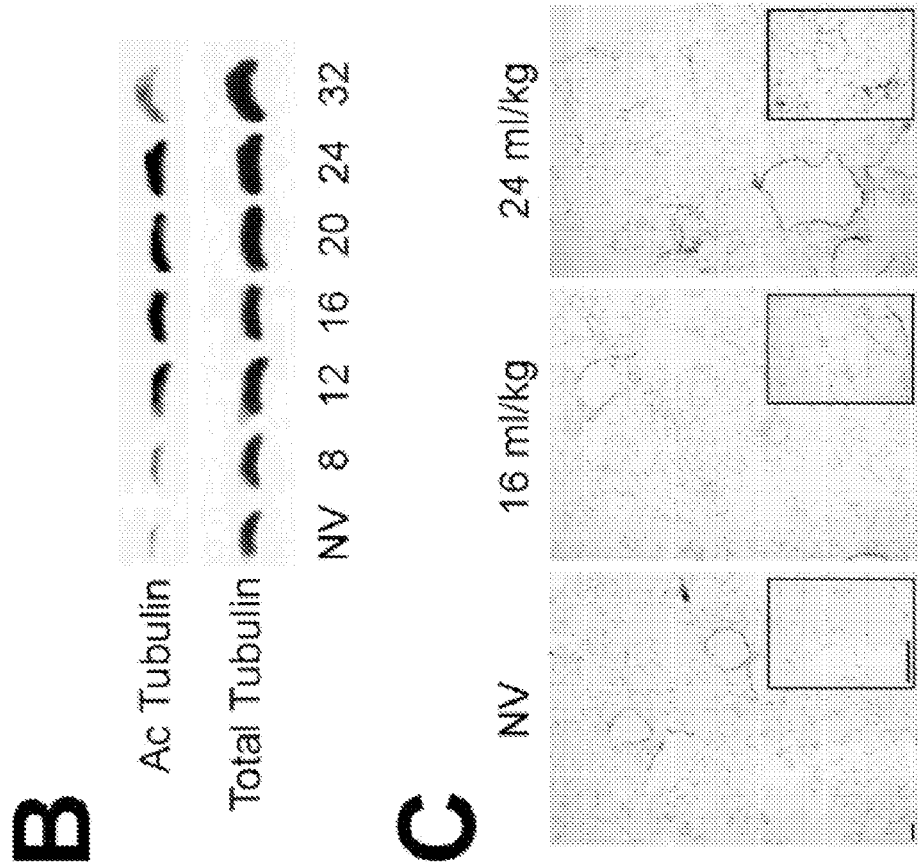
Figure 14:
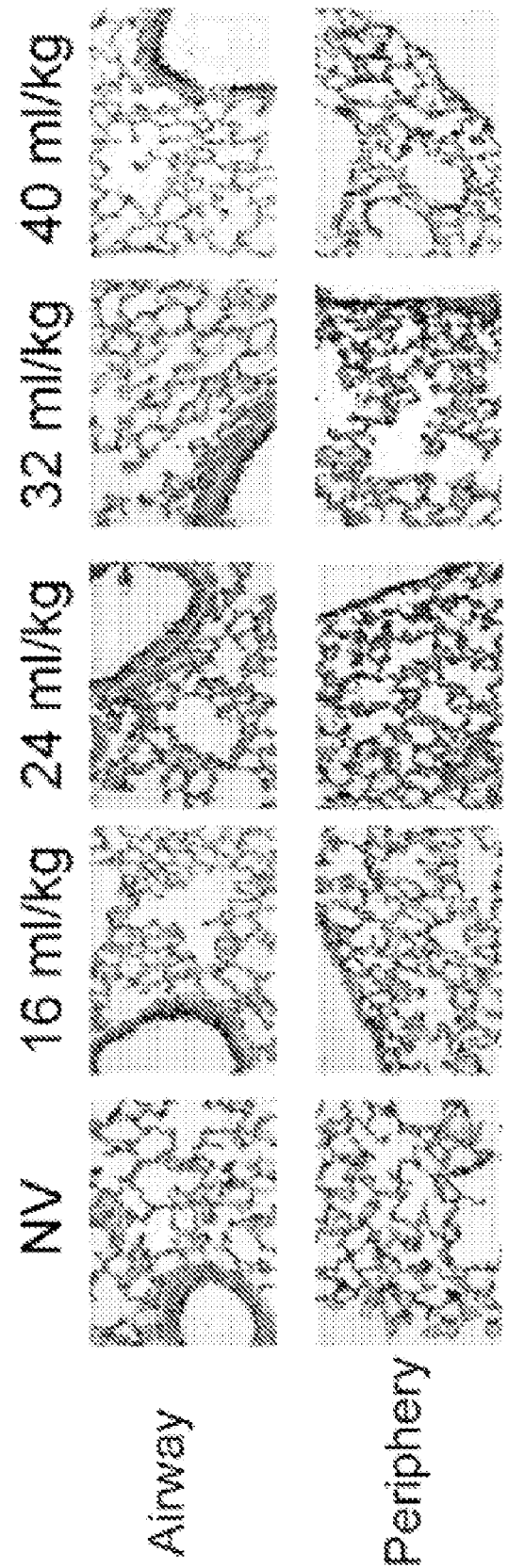
FIG. 14 shows cyclic stretch in vivo results in increased peripheral acetylated tubulin. Female Balb/c mice (18-22 g) were anesthetized and a tracheostomy was performed. Animals were either not mechanically ventilated (NV) or ventilated (Flexivent; SCIREQ Scientific Respiratory Equipment, Inc.; Montreal, Canada) at a tidal volume of 16, 24, 32, and 40 ml/kg and the respiratory rate adjusted to maintain the minute ventilation at 3.5 ml/min for 2 hours, after which lungs were removed and processed for paraffin embedding. Six micron sections were cut and probed for acetylated-tubulin by immunohistochemistry. At the periphery, an increase in brown staining of the airways with increasing tidal volumes indicates increasing amounts of acetylated tubulin.

It has been determined that cyclic stretch increases levels of acetylated microtubules immediately following stretch and causes large-scale depolymerization of unmodified microtubules and actin filaments that persist for at least 24 to 48 hours after the cessation of stretch (17A). To determine whether or not the same type of acetylation events seen in vitro translated to an in vivo setting, animals were either not mechanically ventilated ("NV"), ventilated for 20 minutes followed by 48 hours recovery without mechanical ventilation, or ventilated with increasing tidal volumes for 2 hours and analyzed immediately. As shown in FIG. 13, mice that were ventilated for 20 minutes demonstrate a magnitude-dependent increase in acetylated tubulin that persists for at least 48 hours after the stretch is applied. We used this short period of ventilation followed by a recovery phase based on our previous findings that brief application of cyclic stretch to cultured cells could result in profound changes in cytoskeletal organization that were immediate and persisted over time (FIG. 12 and ref (17A)). Although there was significant variation in the absolute degree of acetylation from animal to animal, accounting for the large standard error in the data points, the same trend was seen for each animal examined (N=4 per condition). Thus, levels of acetylated microtubules increase and remain elevated for at least 48 hours after cessation of ventilation. This increase in acetylated tubulin appears to be primarily in the peripheral lung as assessed by immunohistochemistry. In animals that received no mechanical ventilation, the majority of detected acetylated tubulin is in the airway epithelium, but with increasing tidal volume ventilation, acetylated tubulin appeared in multiple cell types throughout the periphery of lung (FIG. 13C).

To determine whether the levels of acetylate tubulin increase immediately following ventilation or come up slowly over time, animals were ventilated and their lungs removed immediately for analysis by immunohistochemistry (FIG. 3). As seen 48 hours after brief ventilation (FIG. 13C), in lungs that received no mechanical ventilation (NV), the levels of acetylated tubulin are low in the periphery and parenchyma as detected by faint staining of acetylated tubulin throughout the lung section, whereas strong staining is seen in the airway epithelium, primarily in the cilia. However, with 2 hours of stretch, increases in acetylated tubulin are seen immediately, primarily in the parenchyma in alveolar epithelial cells. Qualitatively, the increased immunohistochemical staining correlates well with the increase in acetylated tubulin measured by western blot, with both methods demonstrating a maximal signal at a ventilation volume of 40-60% of total lung capacity (TLC). Taken together, these results demonstrate that cyclic stretch and ventilation cause increases in the levels of acetylated tubulin immediately following ventilation and that these increases persist over time.

HDAC6 siRNA Increases Acetylated Tubulin Levels In Vitro

Having established that stretch causes an increase in acetylated tubulin both in vitro and in vivo, the mechanisms leading to increased tubulin acetylation were examined. The activities of two classes of enzymes can contribute to increased protein acetylation: either an increase in activity of the acetylase enzyme that causes acetylation, or a decrease in the activity of the enzyme that causes deacetylation. Since it is known that HDAC6 deacetylates tubulin (27A), the ability of siRNA against HDAC6 to modulate microtubule acetylation when stretched was examined. This would determine if a mechanism other than HDAC6 modulation was responsible for microtubule acetylation in stretched cells. For this example, stably-transfected A549 cells expressing siRNA against HDAC6 were stretched along with non-siRNA expressing A549 cells. The siRNA-expressing cells show >90% knock-down of HDAC6 protein levels (FIG. 15)(27A). When stretched (10% SA, 0.25 Hz) for 24 hours, the control A549 cells exhibit a 2-fold increase in acetylated tubulin compared to unstretched cells. However, cells expressing HDAC6 siRNA showed no increase in acetylated tubulin over their hyperacetylated state when stretched, suggesting that HDAC6 activity, and not some other unknown process resulting from cyclic stretch, plays an important role in tubulin acetylation in stretched cells.

Stretch Decreases Cytoplasmic HDAC Activity.

Having established that stretch causes an increase in acetylated tubulin and that stretching cells that have decreased HDAC6 activity does not alter the level of microtubule acetylation in vitro, it was sough to determine if stretch caused a decrease in HDAC6 activity. When A549 cells were stretched for 24 hours (10% SA, 0.25 Hz), cytoplasmic HDAC activity, as measured in cytoplasmic extracts, was decreased over 2.5-fold compared to cells that were not stretched (FIG. 16). HDAC6 is the only HDAC that resides almost exclusively in the cytoplasm, and thus a decrease in cytoplasmic HDAC activity should primarily result from a decrease in HDAC6 activity. Therefore it is highly likely that decreased HDAC6 activity is the main mechanism for increased microtubule acetylation in stretched alveolar epithelial cells.

Cyclic Stretch does not Alter Transcription of HDAC6 Targets

Knowing that HDAC6 activity was altered through mechanical stimulation, we next wanted to determine if the levels of HDAC6, other targets of HDAC6, or other HDACs in general were affected at the transcriptional level by stretch. To determine this, mRNA levels of these targets were examined using quantitative polymerase chain reaction (qPCR). In cells that had been stretched for either 3 or 24 hours, none of the examined mRNA levels were increased or decreased by more than a factor of 2, suggesting that any changes in transcription of these genes in response to cyclic stretch is minor. (FIG. 17).

REFERENCES

1. X. Gao and L. Huang (1993). Cytoplasmic expression of a reporter gene by codelivery of T7 RNA polymerase and T7 promoter sequence with cationic liposomes. Nucleic Acids Res 21:2867-72.
2. J. Zabner, A. J. Fasbender, T. Moninger, K. A. Poellinger and M. J. Welsh (1995). Cellular and molecular barriers to gene transfer by a cationic lipid. J Biol Chem 270:18997-9007.
3. H. P. Kao, J. R. Abney and A. S. Verkman (1993). Determinants of the translational mobility of a small solute in cell cytoplasm. J Cell Biol 120:175-84.
4. G. L. Lukacs, P. Haggie, O, Seksek, D. Lechardeur, N. Freedman and A. S. Verkman (2000). Size-dependent DNA mobility in cytoplasm and nucleus. J Biol Chem 275:1625-9.
5. E. Dauty and A. S. Verkman (2005). Actin cytoskeleton as the principal determinant of size-dependent DNA mobility in cytoplasm: a new barrier for non-viral gene delivery. J Biol Chem 280:7823-8.
6. A. Mesika, V. Kiss, V. Brumfeld, G. Ghosh and Z. Reich (2005). Enhanced intracellular mobility and nuclear accumulation of DNA plasmids associated with a karyophilic protein. Hum Gene Ther 16:200-8.
7. E. E. Vaughan and D. A. Dean (2006). Intracellular trafficking of plasmids during transfection is mediated by microtubules. Mol Ther 13:422-8.
8. H. Salman, A. Abu-Arish, S. Oliel, A. Loyter, J. Klafter, R. Granek and M. Elbaum (2005). Nuclear localization signal peptides induce molecular delivery along microtubules. Biophys J 89:2134-45.
9. G. Piperno, M. LeDizet and X. J. Chang (1987). Microtubules containing acetylated alpha-tubulin in mammalian cells in culture. J Cell Biol 104:289-302.
10. S. W. L'Hernault and J. L. Rosenbaum (1985). *Chlamydomonas* alpha-tubulin is posttranslationally modified by acetylation on the epsilon-amino group of a lysine. Biochemistry 24:473-8.
11. M. LeDizet and G. Piperno (1987). Identification of an acetylation site of *Chlamydomonas* alpha-tubulin. Proc Natl Acad Sci USA 84:5720-4.

12. N. A. Reed, D. Cai, T. L. Blasius, G. T. Jih, E. Meyhofer, J. Gaertig and K. J. Verhey (2006). Microtubule acetylation promotes kinesin-1 binding and transport. Curr Biol 16:2166-72.
13. R. C. Geiger, W. Taylor, M. R. Glucksberg and D. A. Dean (2006). Cyclic stretch induced reorganization of the cytoskeleton and its role in enhanced gene transfer. Gene Ther 13:725-31.
14. W. Taylor, K. E. Gokay, C. Capaccio, E. Davis, M. Glucksberg and D. A. Dean (2003). The effects of cyclic stretch on gene transfer in alveolar epithelial cells. Mol Ther 7:542-9.
15. Y. Zhang, N. Li, C. Caron, G. Matthias, D. Hess, S. Khochbin and P. Matthias (2003). HDAC-6 interacts with and deacetylates tubulin and microtubules in vivo. Embo J 22:1168-79.
16. T. Suzuki, A. Kouketsu, Y. Itoh, S. Hisakawa, S. Maeda, M. Yoshida, H. Nakagawa and N. Miyata (2006). Highly potent and selective histone deacetylase 6 inhibitors designed based on small-molecular substrate. J Med Chem 49:4809-4812.
17. G. L. Wilson, B. S. Dean, G. Wang and D. A. Dean (1999). Nuclear import of plasmid DNA in digitonin-permeabilized cells requires both cytoplasmic factors and specific DNA sequences. J. Biol. Chem. 274:22025-22032.
18. J. J. Kovacs, P. J. Murphy, S. Gaillard, X. Zhao, J. T. Wu, C. V. Nicchitta, M. Yoshida, D. O. Toft, W. B. Pratt and T. P. Yao (2005). HDAC6 regulates Hsp90 acetylation and chaperone-dependent activation of glucocorticoid receptor. Mol Cell 18:601-7.
19. M. H. Brush, A. Guardiola, J. H. Connor, T. P. Yao and S. Shenolikar (2004). Deactylase inhibitors disrupt cellular complexes containing protein phosphatases and deacetylases. J Biol Chem 279:7685-91.
20. X. Kong, Z. Lin, D. Liang, D. Fath, N. Sang and J. Caro (2006). Histone deacetylase inhibitors induce VHL and ubiquitin-independent proteasomal degradation of hypoxia-inducible factor 1alpha. Mol Cell Biol 26:2019-28.
21. D. Z. Qian, S. K. Kachhap, S. J. Collis, H. M. Verheul, M. A. Carducci, P. Atadja and R. Pili (2006). Class II Histone Deacetylases Are Associated with VHLlndependent Regulation of Hypoxia-Inducible Factor 1 {alpha}. Cancer Res 66:8814-21.
22. S. H. Kim, J. W. Jeong, J. A. Park, J. W. Lee, J. H. Seo, B. K. Jung, M. K. Bae and K. W. Kim (2007). Regulation of the HIF-1alpha stability by histone deacetylases. Oncol Rep 17:647-51.
23. S. H. Kim, K. W. Kim and J. W. Jeong (2007). Inhibition of hypoxia-induced angiogenesis by sodium butyrate, a histone deacetylase inhibitor, through hypoxiainducible factor-1alpha suppression. Oncol Rep 17:793-7.
24. A. Matsuyama, T. Shimazu, Y. Sumida, A. Saito, Y. Yoshimatsu, D. Seigneurin-Berny, H. Osada, Y. Komatsu, N. Nishino, S. Khochbin, S. Horinouchi and M. Yoshida (2002). In vivo destabilization of dynamic microtubules by HDAC6-mediated deacetylation. Embo J 21:6820-31.
25. J. C. Warren and L. Cassimeris (2007). The contributions of microtubule stability and dynamic instability to adenovirus nuclear localization efficiency. Cell Motil Cytoskeleton 64:675-89.
26. G. J. Dompierre J, Charrin B, Cordelieres F, King S, Humbert S, Saudou F (2007). Histone Deacetylase 6 Inhibition Compensates for the Transport Deficit in Huntington's Disease by Increasing Tubulin Acetylation. The Journal of Neuroscience 21:3571-3583.
27. J. Gardiner, D. Barton, J. Marc and R. Overall (2007). Potential role of tubulin acetylation and microtubule-based protein trafficking in familial dysautonomia. Traffic 8:1145-9.
28. Y. Kawaguchi, J. Kovacs, A. McLaurin, J. Vance, A. Ito and T. Yao (2003). The deacetylase HDAC6 regulates aggresome formation and cell viability in response to misfolded protein stress. Cell 115:727-38.
29. J. Vacik, B. S. Dean, W. E. Zimmer and D. A. Dean (1999). Cell-specific nuclear import of plasmid DNA. Gene Ther 6:1006-14.
30. J. Z. Gasiorowski and D. A. Dean (2005). Postmitotic Nuclear Retention of Episomal Plasmids Is Altered by DNA Labeling and Detection Methods. Mol Ther 12:460-467.
31. D. A. Dean, B. S. Dean, S. Muller and L. C. Smith (1999). Sequence requirements for plasmid nuclear import. Exp Cell Res 253:713-22.
32. B. Lugtenberg, J. Meijers, R. Peters, P. van der Hoek and L. van Alphen (1975). Electrophoretic resolution of the "major outer membrane protein" of *Escherichia coli* K12 into four bands. FEBS Lett 58:254-8.
1A. Corbridge, T. C., L. D. Wood, G. P. Crawford, M. J. Chudoba, J. Yanos, and J. I. Sznajder. 1990. Adverse effects of large tidal volume and low PEEP in canine acid aspiration. Am Rev Respir Dis 142(2):311-5.
2A. Ware, L. B., and M. A. Matthay. 2000. The acute respiratory distress syndrome. N Engl J Med 342(18):1334-49.
3A. Webb, H. H., and D. F. Tierney. 1974. Experimental pulmonary edema due to intermittent positive pressure ventilation with high inflation pressures. Protection by positive end-expiratory pressure. Am Rev Respir Dis 110 (5):556-65.
4A. ARDS Network. 2000. Ventilation with lower tidal volumes as compared with traditional tidal volumes for acute lung injury and the acute respiratory distress syndrome. The Acute Respiratory Distress Syndrome Network. N Engl J Med 342(18):1301-8.
5A. Ricard, J., D. Dreyfuss, and G. Saumon. 2003. Ventilator-induced lung injury. Eur Respir J Supplement 42:2s-9s.
6A. Hammerschmidt, S., H. Kuhn, T. Grasenack, C. Gessner, and H. Wirtz. 2003. Apoptosis and necrosis induced by cyclic mechanical stretching in alveolar type II cells. Am J Respir Cell Mol Biol 30(3):396-402.
7A. Trepat, X., F. Puig, J. Gavara, J. J. Fredberg, R. Farre, and D. J. Navajas. 2006. Effect of stretch on structural integrity and micromechanics of human alveolar epithelial cell monolayers exposed to thrombin. Am J Physiol Lung Cell Mol Physiol 290(6):L1104-L1110.
8A. Vlahakis, N., M. Schroeder, R. Pagano, and R. D. Hubmayr. 2001. Deformation-induced lipid trafficking in alveolar epithelial cells. Am J Physiol Lung Cell Mol Physiol 208(5):L938-L946.
9A. Chapman, K. E., S. E. Sinclair, D. Zhuang, A. Hassid, L. P. Desai, and C. M. Waters. 2005. Cyclic mechanical strain increases reactive oxygen species production in pulmonary epithelial cells. Am J Physiol Lung Cell Mol Physiol 289: L834-L841.
10A. Papaiahgari, S., A. Yerrapureddy, P. Hassoun, J. Garcia, K. Birukov, and S. Reddy. 2006. EGFR-Activated Signaling and Actin Remodeling Regulate Cyclic Stretch-Induced NRF2-ARE Activation. Am J Respir Cell Mol Biol 36(3):304-312.
11A. Pugin, J. 2003. Molecular mechanisms of lung cell activation induced by cyclic stretch. Crit. Care Med 31(4 Supplement):5200-5206.

12A. Wirtz, D., and L. Dobbs. 2000. The effects of mechanical forces on lung functions. Respir Physiol 119(1):1-17.
13A. Schumacker, P. T. 2002. Straining to understand mechanotransduction in the lung. Am J Physiol Lung Cell Mol Physiol 282(5):L881-L882.
14A. Tschumperlin, D. J., J. Oswari, and A. S. Margulies. 2000. Deformation induced injury of alveolar epithelial cells. Effect of frequency, duration, and amplitude. Am J Respir Crit. Care Med 162(2 Pt 1):357-62.
15A. Liu, M., and M. Post. 2000. Mechanochemical signal transduction in the fetal lung. J Appl Physiol 89(5):2078-84.
16A. Hayakawa, K., N. Sato, and T. Obinata. 2001. Dynamic reorientation of cultured cells and stress fibers under mechanical stress from periodic stretching. Exp Cell Res 268(1):104-14.
17A. Geiger, R. C., W. Taylor, M. R. Glucksberg, and D. A. Dean. 2006. Cyclic stretch-induced reorganization of the cytoskeleton and its role in enhanced gene transfer. Gene Ther 13(8):725-31.
18A. Putnam, A. J., K. Schultz, and D. J. Mooney. 2001. Control of microtubule assembly by extracellular matrix and externally applied strain. Am J Physiol Cell Physiol 280(3):C556-64.
19A. Ridge, K., L. Linz, F. Flitney, E. Kuczmarski, Y. Chou, M. Omary, J. I. Sznajder, and R. D. Goldman. 2005. Keratin 8 phosphorylation by protein kinase C delta regulates shear stress-mediated disassembly of keratin intermediate filaments in alveolar epithelial cells. J Biol Chem 280(34): 30400-30405.
20A. Smith, P., R. Garcia, and L. Kogerman. 1997. Strain reorganizes focal adhesions and cytoskeleton in cultured airway smooth muscle cells. Exp Cell Res 232(1):127-136.
21A. Apodaca, G. L. 2002. Modulation of membrane traffic by mechanical stimuli. Am J Physiol Renal Physiol 282(2): F179-F190.
22A. Lehoux, S., and A. Tedgui. 2003. Cellular mechanics and gene expression in blood vessels. J Biomech 36(5): 631-643.
23A. Westermann, S., and K. Weber. 2003. Post-translational modifications regulate microtubule function. Nat Rev Mol Cell Biol 4(12):938-47.
24A. L'Hernault, S., and J. Rosenbaum. 1985. *Chlamydomonas* alpha-tubulin is posttranslationally modified by acetylation on the epsilon-amino group of a lysine. Biochemistry 24(2):473-478.
25A. Billger, M., E. Stromberg, and M. Wallin. 1991. Microtubule-associated proteins-dependent colchicine stability of acetylated cold-labile brain microtubules from the Atlantic cod, Gadus morhua. J Cell Biol 113(2):331-318.
26A. Haggarty, S., K. Koeller, J. Wong, C. Grozinger, and S. L. Schreiber. 2003. Domain-selective small-molecule inhibitor of histone deacetylase 6 (HDAC6)-mediated tubulin deacetylation. Proc Natl Acad Sci USA 100(8): 4389-4394.
27A. Hubbert, C., A. Guardiola, R. Shao, Y. Kawaguchi, A. Ito, A. Nixon, M. Yoshida, X. F. Wang, and T. P. Yao. 2002. HDAC6 is a microtubule-associated deacetylase. Nature 417(6887):455-8.
28A. Matsuyama, A., T. Shimazu, Y. Sumida, A. Saito, Y. Yoshimatsu, D. Seigneurin-Berny, H. Osada, Y. Komatsu, N. Nishino, S. Khochbin, S. Horinouchi, and M. Yoshida. 2002. In vivo destabilization of dynamic microtubules by HDAC6-mediated deacetylation. Embo J 21(24):6820-31.
29A. Palazzo, A., B. Ackerman, and G. G. Gundersen. 2003. Cell biology: Tubulin acetylation and cell motility. Nature 421(6920):230.
30A. Reed, N., D. Cai, T. Blasius, G. Jih, E. Meyhofer, J. Gaertig, and K. Verhey. 2006. Microtubule acetylation promotes kinesin-1 binding and transport. Curr Biol 16(21): 2166-2172.
31A. Bulinski, J. C. 2007. Microtubule modification: acetylation speeds anterograde traffic flow. Curr Biol 17(1): R18-R20.
32A. Dompierre, J. P., J. D. Godin, B. C. Charrin, F. P. Cordelieres, S. J. King, S. Humbert, and F. Saudou. 2007. Histone deacetylase 6 inhibition compensates for the transport deficit in Huntington's disease by increasing tubulin acetylation. J. Neurosci 27(13):3571-83.
33A. Kawaguchi, Y., J. J. Kovacs, A. McLaurin, J. M. Vance, A. Ito, and T. P. Yao. 2003. The deacetylase HDAC6 regulates aggresome formation and cell viability in response to misfolded protein stress. Cell 115(6):727-38.
34A. Caron, J. M., A. L. Jones, and M. W. Kirschner. 1985. Autoregulation of tubulin synthesis in hepatocytes and fibroblasts. J Cell Biol 101(5):1763-1772.
35A. Lai, Y.-L., and H.-C. Chou. 2000. Respiratory mechanics and maximal expiratory flow in the anesthetized mouse. J Appl Physiol 88:939-943.
36A. Adam, S. A., R. S. Marr, and L. Gerace. 1990. Nuclear protein import in permeabilized mammalian cells requires soluble cytoplasmic factors. J. Cell Biol. 111:807-816.
37A. Birukov, K. G., J. R. Jacobson, A. A. Flores, S. Q. Ye, A. A. Birukova, A. D. Verin, and J. G. Garcia. 2003. Magnitude-dependent regulation of pulmonary endothelial cell barrier function by cyclic stretch. Am J Physiol Lung Cell Mol Physiol 285(4):L785-L797.
38A. Birukova, A. A., K. Birukov, B. Gorshkov, F. Liu, J. G. Garcia, and A. D. Verin. 2005. MAP kinases in lung endothelial permeability induced by microtubule disassembly. Am J Physiol Lung Cell Mol Physiol 289(1):L75-L84.
39A. Tschumperlin, D. J., and A. S. Margulies. 1998. Equibiaxial deformation induced injury of alveolar epithelial cells in vitro. Am J Physiol Lung Cell Mol Physiol 275: L1173-L1183.
40A. Taylor, W., K. E. Gokay, C. Capaccio, E. Davis, M. R. Glucksberg, and D. A. Dean. 2003. Effects of cyclic stretch on gene transfer in alveolar epithelial cells. Mol Ther 7(4): 542-9.
41A. Belperio, J. A., M. P. Keane, M. D. Burdick, V. Londhe, Y. Y. Xue, K. Li, R. J. Phillips, and R. M. Strieter. 2002. Critical role for CXCR2 and CXCR2 ligands during the pathogenesis of ventilator-induced lung injury. J Clin Invest 110(11):1703-16.
42A. Kaynar, A. M., A. M. Houghton, E. H. Lum, B. R. Pitt, and S. D. Shapiro. 2008. Neutrophil Elastase 1s Needed for Neutrophil Emigration into Lungs in Ventilator-Induced Lung Injury. Am J Respir Cell Mol. Biol.
43A. Simon, B. A., R. B. Easley, D. N. Grigoryev, S.-F. Ma, S. Q. Ye, T. Lavoie, R. M. Tuder, and J. G. N. Garcia. 2006. Microarray analysis of regional cellular responses to local mechanical stress in acute lung injury. Am J Physiol Lung Cell Mol Physiol 291(5):L851-861.
44A. Tremblay, L., F. Valenza, S. P. Ribeiro, J. Li, and A. S. Slutsky. 1997. Injurious ventilatory strategies increase cytokines and c-fos m-RNA expression in an isolated rat lung model. J Clin Invest 99(5):944-52.
45A. Brangwynne, C. P., F. C. MacKintosh, S. Kumar, N. A. Geisse, J. Talbot, L. Mahadevan, K. K. Parker, D. E. Ingber, and D. A. Weitz. 2006. Microtubules can bear enhanced compressive loads in living cells because of lateral reinforcement. J Cell Biol 173(5):733-741.

46A. Felgner, H., R. Frank, and M. Schliwa. 1996. Flexural rigidity of microtubules measured with the use of optical tweezers. J Cell Sci 109(2):509-516.

47A. Kikumoto, M., M. Kurachi, V. Tosa, and H. Tashiro. 2006. Flexural rigidity of individual microtubules measured by a buckling force with optical traps. Biophys J 90(5):1687-1696.

48A. Takemura, R., S. Okabe, T. Umeyama, Y. Kanai, N. J. Cowan, and N. Hirokawa. 1992. Increased microtubule stability and alpha tubulin acetylation in cells transfected with microtubule-associated proteins MAP1B, MAP2, or tau. J Cell Sci 103:953-964.

49A. Trepat, X., L. Deng, S. S. An, D. J. Navajas, D. J. Tschumperlin, W. T. Gerthoffer, J. P. Butler, and J. J. Fredberg. 2007. Universal physical responses to stretch in the living cell. Nature 447:592-595.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for increasing nucleic acid expression in cells comprising:
   a) providing:
      i) a gene transfer system, wherein said gene transfer system comprises lipids,
      ii) a specific inhibitor of major tubulin deacetylase 6 (HDAC6), wherein said specific inhibitor inhibits HDAC6 without inhibiting other HDACs,
      iii) mammalian cells, and
      iv) a vector, and
   b) contacting said cells with said vector and said specific inhibitor of HDAC6 in the presence of said gene transfer system such that gene expression from said vector is increased at least 2.5 fold in the presence of said specific inhibitor of HDAC6 compared to expression when said specific inhibitor of HDAC6 is absent, wherein said cells are contacted with said specific inhibitor of HDAC6 together with, or immediately after said contacting with, said vector.

2. The method of claim 1, wherein the gene transfer system comprises an electroporation system.

3. The method of claim 1, wherein the gene transfer system is calcium chloride.

4. The method of claim 1, wherein the gene transfer system is DEAE/dextran.

5. The method of claim 1, wherein said specific inhibitor of HDAC6 is compound 17b.

6. The method of claim 1, wherein said cells are in vitro.

7. The method of claim 1, wherein said cells are in vivo.

* * * * *